US011185281B2

(12) United States Patent
    Garcia Molina et al.

(10) Patent No.: US 11,185,281 B2
(45) Date of Patent: Nov. 30, 2021

(54) SYSTEM AND METHOD FOR DELIVERING SENSORY STIMULATION TO A USER BASED ON A SLEEP ARCHITECTURE MODEL

(71) Applicant: KONINKLIJKE PHILIPS N.V., Eindhoven (NL)

(72) Inventors: Gary Nelson Garcia Molina, Madison, WI (US); Birpal Singh Sachdev, Delmont, PA (US); William Gaussa, Jeannette, PA (US); David White, Denver, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 16/278,901

(22) Filed: Feb. 19, 2019

(65) Prior Publication Data

US 2019/0254591 A1   Aug. 22, 2019

Related U.S. Application Data

(60) Provisional application No. 62/632,594, filed on Feb. 20, 2018.

(51) Int. Cl.
    *A61B 5/00*      (2006.01)
    *G06N 20/00*    (2019.01)
    (Continued)

(52) U.S. Cl.
    CPC .............. *A61B 5/4812* (2013.01); *A61B 5/00* (2013.01); *A61B 5/369* (2021.01); *A61B 5/4809* (2013.01);
    (Continued)

(58) Field of Classification Search
    CPC ....... A61B 5/4812; A61B 5/4809; A61B 5/00; A61B 5/0476; A61M 21/00; G16H 20/30; G16H 50/70; G06F 17/18; G06N 20/00
    See application file for complete search history.

(56) References Cited

U.S. PATENT DOCUMENTS 10,098,582 B1 * 10/2018 McNair ................ A61B 5/7264
10,137,276 B2   11/2018 Garcia Molina et al.
(Continued)

FOREIGN PATENT DOCUMENTS

WO    2015118415 A1    8/2015
WO    2018001936 A1    1/2018

OTHER PUBLICATIONS

International Search Report and Written Opinion, International Application No. PCT/EP2019-054182, dated May 8, 2019.
(Continued)

*Primary Examiner* — Lynsey C Eiseman
*Assistant Examiner* — Amanda L Steinberg

(57) ABSTRACT

The present disclosure pertains to a system and method for providing sensory stimulation (e.g., tones and/or other sensory stimulation) during sleep. The delivery of the sensory stimulation is timed based on a combination of output from a trained time dependent sleep stage model and output from minimally obtrusive sleep monitoring devices (e.g. actigraphy devices, radar devices, video actigraphy devices, an under mattress sensor, etc.). The present disclosure describes determining whether a user is in deep sleep based on this information and delivering sensory stimulation responsive to the user being in deep sleep. In some embodiments, the system comprises one or more sensory stimulators, one or more hardware processors, and/or other components.

15 Claims, 14 Drawing Sheets

(51) Int. Cl.
   *G06F 17/18* (2006.01)
   *G16H 20/30* (2018.01)
   *A61M 21/00* (2006.01)
   *G16H 50/70* (2018.01)
   *A61B 5/369* (2021.01)

(52) U.S. Cl.
   CPC ............ *A61M 21/00* (2013.01); *G06F 17/18* (2013.01); *G06N 20/00* (2019.01); *G16H 20/30* (2018.01); *G16H 50/70* (2018.01)

(56) References Cited

U.S. PATENT DOCUMENTS

| | | | |
|---|---|---|---|
| 10,183,142 B2 | 1/2019 | Garcia Molina et al. | |
| 2016/0082222 A1 | 3/2016 | Garcia Molina et al. | |
| 2016/0296164 A1 | 10/2016 | Garcia Molina | |
| 2016/0302718 A1 | 10/2016 | Laura Lapoint et al. | |
| 2017/0055899 A1* | 3/2017 | Bandyopadhyay | A61B 5/02055 |
| 2018/0064388 A1* | 3/2018 | Heneghan | A61B 5/7264 |
| 2018/0238103 A1* | 8/2018 | Jensen | E06B 3/6736 |
| 2020/0222699 A1* | 7/2020 | de Zambotti | A61B 5/4812 |

OTHER PUBLICATIONS

Sathyanarayana, A. et al., "Sleep Quality Prediction From Wearable Data Using Deep Learning", JMIR MHEALTH and UHEALTH, vol. 4, issue 4, 2016.

H.-V. V Ngo, A. Miedema, I. Faude, T. Martinetz, M. Molle, and J. Born, "Driving Sleep Slow Oscillations by Auditory Closed-Loop Stimulation—A Self-Limiting Process," J. Neurosci., vol. 35, No. 17, pp. 6630-6638, 2015.

M. Bellesi, B. A. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.

G. Garcia-Molina, M. Bellesi, S. Pastoor, S. Pfundtner, B. A. Riedner, and G. Tononi, "Online Single EEG Channel Based Automatic Sleep Staging," in Engineering Psychology and Cognitive Ergonomics. Applications and Services, D. Harris, Ed. Springer Berlin Heidelberg, 2013, pp. 333-342.

L. de Souza, A. A. Benedito-Silva, M. L. N. Pires, D. Poyares, S. Tufik, and H. M. Calil, "Further validation of actigraphy for sleep studies.," Sleep, vol. 26, No. 1, pp. 81-85, 2003.

\* cited by examiner

SYSTEM AND METHOD FOR DELIVERING SENSORY STIMULATION TO A USER BASED ON A SLEEP ARCHITECTURE MODEL

CROSS-REFERENCE TO PRIOR APPLICATIONS

This application claims the benefit of U.S. Provisional Application No. 62/632,594, filed on 20 Feb. 2018. This application is hereby incorporated by reference herein.

BACKGROUND

1. Field

The present disclosure pertains to a system and method for facilitating delivery of sensory stimulation to a user during deep sleep in a sleep session.

2. Description of the Related Art

Systems for monitoring sleep and delivering sensory stimulation to users during sleep are known. Both electroencephalogram (EEG) sensor based and non-EEG sensor based sleep monitoring and sensory stimulation systems are known. EEG sensor based systems include EEG sensors often coupled to the scalp of a user. Given that the sleep process is primarily characterized by the electrical activity of the brain, EEG sensor based systems typically generate more accurate information about a sleeping subject compared to non-EEG sensor based systems. However, the non-EEG sensor based system are less intrusive and more comfortable for users because they do not include such EEG sensors and associated wiring that are common to EEG sensor based systems. There is a need for a system that is able to generate accurate information about a sleeping subject relative to prior art systems while still maintaining user comfort during use of the system.

SUMMARY

Accordingly, one or more aspects of the present disclosure relate to a system configured to deliver sensory stimulation to a user during deep sleep in a sleep session. The system comprises one or more sensory stimulators configured to provide sensory stimulation to the user during the sleep session, one or more hardware processors, and/or other components. The one or more hardware processors are coupled to the one or more sensory stimulators. The processors are configured by machine-readable instructions. The processors are configured to obtain historical sleep depth information for a user and/or a population of users. The historical sleep depth information is related to brain activity of the user and/or population of users that indicates sleep depth over time during sleep sessions of the user and/or the population of users. The processors are configured to cause a prediction model to be trained based on the historical sleep depth information by providing the historical sleep depth information as input to the prediction model. The processors are configured to cause the trained prediction model to output a time dependent predicted sleep stage for the user during the sleep session. The time dependent predicted sleep stage indicates whether the user is in deep enough sleep for stimulation. The processors are configured to cause the one or more sensory stimulators to provide the sensory stimulation to the user based on the time dependent predicted sleep stage over time during the sleep session. The sensory stimulators are caused to provide the sensory stimulation to the user responsive to the time dependent predicted sleep stage indicating the user is in deep enough sleep for stimulation. In some embodiments, the processors are configured to receive information from an external sleep monitoring device indicating an estimated sleep stage over time for the user during the sleep session, and cause the one or more sensory stimulators to provide the sensory stimulation based on the estimated sleep stage and the predicted sleep stage over time during the sleep session.

Another aspect of the present disclosure relates to a method for delivering sensory stimulation to a user during deep sleep in a sleep session with a delivery system. The system comprises one or more sensory stimulators configured to provide sensory stimulation to the user during the sleep session, one or more hardware processors configured by machine-readable instructions, and/or other components. The method comprises obtaining, with the one or more hardware processors, historical sleep depth information for a user and/or a population of users. The historical sleep depth information is related to brain activity of the user and/or the population of users that indicates sleep depth over time during sleep sessions of the user and/or the population of users. The method comprises causing, with the one or more hardware processors, a prediction model to be trained based on the historical sleep depth information by providing the historical sleep depth information as input to the prediction model. The method comprises causing, with the one or more hardware processors, the trained prediction model to output a time dependent predicted sleep stage for the user during the sleep session. The time dependent predicted sleep stage indicates whether the user is in deep enough sleep for stimulation. The method comprises causing, with the one or more hardware processors, the one or more sensory stimulators to provide the sensory stimulation to the user based on the time dependent predicted sleep stage over time during the sleep session. The one or more sensory stimulators are caused to provide the sensory stimulation to the user responsive to the time dependent predicted sleep stage indicating the user is in deep enough sleep for stimulation. In some embodiments, the method comprises receiving, with the one or more hardware processors, information from an external sleep monitoring device indicating an estimated sleep stage over time for the user during the sleep session, and causing the one or more sensory stimulators to provide the sensory stimulation based on the estimated sleep stage and the predicted sleep stage over time during the sleep session.

Yet another aspect of the present disclosure relates to a system for delivering sensory stimulation to a user during deep sleep in a sleep session. The system comprises means for providing sensory stimulation to the user during the sleep session. The system comprises means for obtaining historical sleep depth information for a user and/or a population of users. The historical sleep depth information is related to brain activity of the user and/or the population of users that indicates sleep depth over time during sleep sessions of the user and/or the population of users. The system comprises means for causing a prediction model to be trained based on the historical sleep depth information by providing the historical sleep depth information as input to the prediction model. The system comprises means for causing the trained prediction model to output a time dependent predicted sleep stage for the user during the sleep session. The time dependent predicted sleep stage indicates whether the user is in deep enough sleep for stimulation. The system comprises means for causing the means for providing sensory stimulation to provide the sensory stimulation to the user based on the time dependent predicted sleep stage over time during the sleep session. The means for providing sensory stimulation is caused to provide the sensory stimulation to the user responsive to the time dependent predicted sleep stage indicating the user is in deep enough sleep for stimulation. In some embodiments, the system further comprises means for receiving information from an external sleep monitoring device indicating an estimated sleep stage over time for the user during the sleep session, and causing the means for generating sensory stimulation to provide the sensory stimulation based on the estimated sleep stage and the predicted sleep stage over time during the sleep session.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
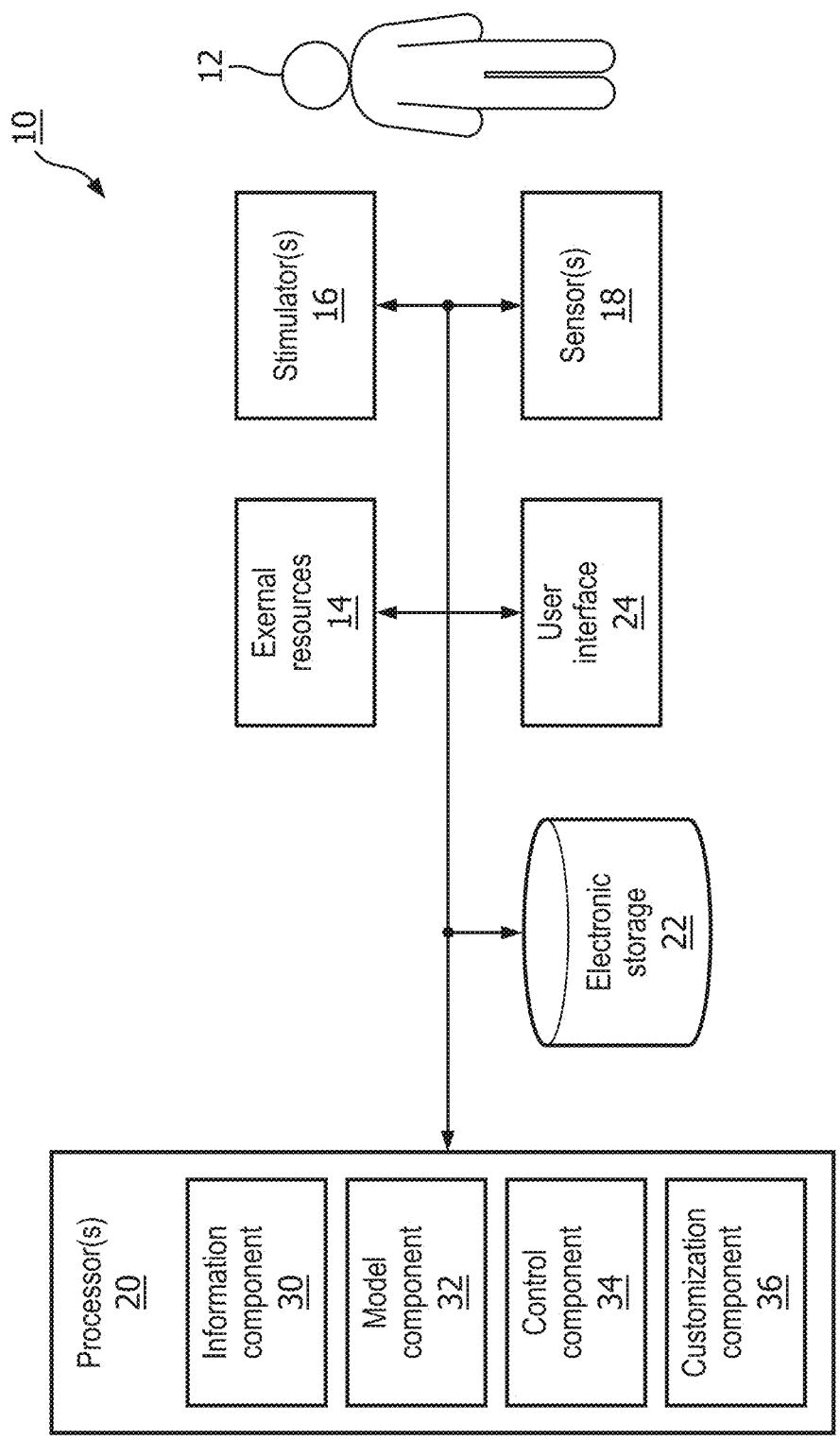
FIG. 1 is a schematic illustration of a system configured to facilitate delivery of sensory stimulation to a user during deep sleep in a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to facilitate delivery of sensory stimulation to a user 12 to enhance the restorative effects of sleep in user 12 and/or for other purposes. In some embodiments, system 10 includes one or more of external resources 14, a sensory stimulator 16, a processor 20, electronic storage 22, a user interface 24, and/or other components. In some embodiments, system 10 includes one or more sensors 18. System 10 is configured such that sensory stimulation including auditory and/or other stimulation delivered during sleep enhances slow waves in user 12 without causing arousals, which brings cognitive benefits and enhancement of sleep restoration, for example. As described herein, in some embodiments, system 10 is configured to determine periods of deep sleep during a sleep session (e.g., based on output from a prediction model, information from external sleep monitoring devices, and/or other information). In some embodiments, based on such determinations, system 10 is configured to deliver sensory (e.g., auditory) stimulation to enhance sleep slow waves without causing arousals. In some embodiments, periods of deep sleep may be determined in real-time and/or near real-time during a sleep session of user 12.

Electroencephalogram (EEG) sensor based sleep data for a large population of users (historical sleep depth information) is available from various sources (e.g., included in external resources 14 described below). The EEG-based sleep data may include, for example, information included in EEG sensor output signals for users of prior art sleep monitoring systems, and/or other information. In some embodiments, system 10 is configured to analyze this data and, based on such data and/or analysis, provide a prediction model for sleep architecture dynamics (e.g., sleep stage sequence) and sleep depth (e.g., delta to beta and delta to alpha ratios as described herein) dynamics for sleep sessions. This prediction model is used by system 10 to predict periods of deep sleep in user 12 for delivery of sensory stimulation. Additionally, or alternatively, the prediction model is used to anticipate sleep stage transitions in response to the stimulation as described herein. In some embodiments, system 10 is configured to combine output from the prediction model with information from existing non-EEG sensor based external sleep monitoring devices (e.g., wrist actigraphy devices, video based actigraphy devices, audio sleep monitoring devices, bed motion sensor devices, electrocardiogram (ECG) devices, photoplethysmography (PPG) devices, etc.) that are less intrusive than a typical EEG sensor based system, but also less accurate than the EEG based systems, to determine deep sleep in user 12 and/or timing for sensory stimulation. Accuracy in this context is quantified by a sleep stage detection error compared to ground truth (i.e., manual scoring by an expert sleep technician). For instance, it is well known that with actigraphy only sleep and wake states can be detected and specific states such as deep sleep or REM sleep cannot be detected with actigraphy. In some embodiments, system 10 is configured to determine deep sleep and/or the timing of sensory stimulation without receiving information from an external sleep monitoring device (e.g., deep sleep and/or the timing of sensory stimulation is based on the output of the prediction model alone) or without using such external sleeping monitoring device information for such determinations.

External resources 14 include sources of information (e.g., databases, websites, etc.), external entities participating with system 10 (e.g., one or more the external sleep monitoring devices, a medical records system of a health care provider, etc.), and/or other resources. For example, external resources 14 may include sources of historical sleep depth information for a population of users, and/or other information. The historical sleep depth information for the population of users may be related to brain activity of the population of users that indicates sleep depth over time during sleep sessions of the population of users. In some embodiments, the information related to brain activity that indicates sleep depth over time is information related to slow wave activity in the population of users.

In some embodiments, the slow wave activity of the population of users may be used to determine sleep stages of the population of users for corresponding sleep sessions. The sleep stages of the population of users may be associated with rapid eye movement (REM) sleep, non-rapid eye movement (NREM) sleep, and/or other sleep. The sleep stages of the population of users may be one or more of NREM stage N1, stage N2, or stage N3, REM sleep, and/or other sleep stages. In some embodiments, the sleep stages of the population of users may be one or more of stage S1, S2, S3, or S4. In some embodiments, NREM stage 2 and/or 3 (and/or S3 and/or S4) may be slow wave (e.g., deep) sleep. In some embodiments, the information related to brain activity that indicates sleep depth over time is and/or is related to one or more additional brain activity parameters for the population of users.

In some embodiments, the information related to brain activity that indicates sleep depth over time is and/or includes EEG information generated during sleep sessions of the population of users. In some embodiments, brain activity parameters may be determined based on the EEG information. In some embodiments, the brain activity parameters may be determined by processor 20 and/or other components of system 10. In some embodiments, the brain activity parameters may be previously determined and be part of the historical sleep depth information obtained from external resources 14. In some embodiments, the one or more brain activity parameters are and/or are related to a frequency, amplitude, phase, presence of specific sleep patterns such as spindles, K-complexes, or sleep slow waves, alpha waves, and/or other characteristics of an EEG signal.

In some embodiments, the one or more brain activity parameters are determined based on the frequency, amplitude, and/or other characteristics of the EEG signal. In some embodiments, the determined brain activity parameters and/or or the characteristics of the EEG may be and/or indicate sleep stages that correspond to the REM and/or NREM sleep stages described above. For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-12 Hz band) is no longer present and slow waves are not present. In some embodiments, slow wave activity is a continuous value (e.g., EEG power in the 0.4 to 4 Hz band), which is positive. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and SWA are the same when considering sleep EEG. In some embodiments, the information related to brain activity that indicates sleep depth over time indicates changes in an EEG delta power over time, a quantity of micro arousals in the population of users, other EEG power levels, and/or other parameters.

In some embodiments, the historical sleep depth information for the population of users may be related to a user population in a given geographical area; demographic information related to gender, ethnicity, age, a general health level, and/or other demographic information; physiological information (e.g., weight, blood pressure, pulse, etc.) about the population of users, and/or other information. In some embodiments, this information may indicate whether an individual user in the population of user is demographically, physiologically, and/or otherwise similar to user 12.

In some embodiments, external resources 14 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 14 may be provided by resources included in system 10. External resources 14 may be configured to communicate with processor 20, user interface 24, sensor 18, electronic storage 22, sensory stimulator 16, and/or other components of system 10 via wired and/or wireless connections, via a network (e.g., a local area network and/or the internet), via cellular technology, via Wi-Fi technology, and/or via other resources.

Sensory stimulator 16 is configured to provide sensory stimulation to user 12. Sensory stimulator 16 is configured to provide auditory, visual, somatosensory, electric, magnetic, and/or sensory stimulation to user 12 prior to a sleep session, during a sleep session, and/or at other times. In some embodiments, a sleep session may comprise any period of time when user 12 is sleeping and/or attempting to sleep. Sleep sessions may include nights of sleep, naps, and/or other sleeps sessions. For example, sensory stimulator 16 may be configured to provide stimuli to user 12 during a sleep session to facilitate a transition to a deeper stage of sleep, a lighter stage of sleep, maintain sleep in a specific stage, enhance the restorative effects of sleep, and/or for other purposes. In some embodiments, sensory stimulator 16 may be configured such that facilitating a transition between deeper sleep stages and lighter sleep stages includes decreasing sleep slow waves in user 12, and facilitating a transition between lighter sleep stages and deeper sleep stages includes increasing sleep slow waves.

Sensory stimulator 16 is configured to facilitate transitions between sleep stages, maintain sleep in a specific stage, and/or enhance the restorative effects of sleep through non-invasive brain stimulation and/or other methods. Sensory stimulator 16 may be configured to facilitate transitions between sleep stages, maintain sleep in a specific stage, and/or enhance the restorative effects of sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. For example, acoustic tones may be provided to user 12 to enhance the restorative effects of sleep in user 12. The acoustic tones may include one or more series of 50-millisecond long tones separated from each other by a fixed 1-second long intertone interval. The volume of individual tones may be modulated by sleep depth such that loud (soft) tones are played during deeper (shallower) sleep. This example is not intended to be limiting. Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to user 12.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a customization component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to obtain historical sleep depth information. The historical sleep depth information is for a population of users. The historical sleep depth information is related to brain activity of the population of users that indicates sleep depth over time during sleep sessions of the population of users.

As described above, the historical sleep depth information is related to sleep stages and/or other brain activity parameters of the population of users during corresponding sleep sessions, and/or other information related to the population of users. In some embodiments, information component 30 is configured to obtain the historical sleep depth information electronically from external resources 14, electronic storage 22, and/or other sources of information. In some embodiments, obtaining the historical sleep depth information electronically from external resources 14, electronic storage 22, and/or other sources of information comprises querying one more databases and/or servers; uploading information and/or downloading information, facilitating user input (e.g., criteria used to define a target patient population input via user interface 24), sending and/or receiving emails, sending and/or receiving text messages, and/or sending and/or receiving other communications, and/or other obtaining operations. In some embodiments, information component 30 is configured to aggregate information from various sources (e.g., one or more of the external resources 14 described above, electronic storage 22, etc.), arrange the information in one or more electronic databases (e.g., electronic storage 22, and/or other electronic databases), normalize the information based on one or more features of the historical sleep depth information (e.g., length of sleep sessions, number of sleep sessions, etc.) and/or perform other operations.

In some embodiments, information component 30 is configured to obtain, receive, and/or determine information from an external sleep monitoring device (e.g., included in external resources 14) that indicates an estimated sleep stage of the user. The information from the external sleep monitoring device may be received over time during the sleep session and/or at other times. In some embodiments, the information from the external sleep monitoring devices may be included in output signals generated by such devices, stored in electronic storage in such devices, transmitted (e.g., via a network and/or other transmission components) by such devices, and/or include other information. In some embodiments, information component 30 is configured to obtain, receive, and/or determine information from an external sleep monitoring device directly and/or indirectly. For example, information component 30 may be configured to receive information from an external sleep monitoring device via a transmitted signal directly from such a device. As another example, information component 30 may, wirelessly and/or via wires, query electronic storage that is part of the device, network connected databases associated with such devices, and/or other sources of information associated with an external sleep monitoring device. In some embodiments, the information from the external sleep monitoring devices indicates a current sleep stage of user 12 and/or other information related to brain activity in user 12 (e.g., a given external sleep monitoring device makes the determination). In some embodiments, information component 30 is configured to determine a sleep stage of user 12 based on the information from the external sleep monitoring devices (e.g., based on information in output signals generated by a given external sleep monitoring device). The information from the external sleep monitoring devices may include wrist (and/or other limb) actigraphy sleep stage and/or other information, video based actigraphy sleep stage and/or other information, audio sleep monitoring sleep stage and/or other information, bed motion sensor sleep stage and/or other information, ECG sleep stage and/or other information, PPG sleep stage and/or other information, and/or other information.

Model component 32 is configured to cause a prediction model to be trained using the historical sleep depth information. In some embodiments, the prediction model may be and/or include mathematical equations, plots, charts, networks (e.g., recurrent neural networks, multiresolution recurrent neural networks, etc.), a regression model, machine learning algorithms, a linear models, rules based and/or probabilistic models, and/or other prediction models. In some embodiments, the prediction model is trained based on the historical sleep depth information by providing the historical sleep depth information as input to the prediction model. In some embodiments, causing the prediction model to be trained comprises determining, by model component 32, average sleep depth and a probability of a particular sleep stage over time for a given sleep session based on the historical sleep depth information for the sleep sessions of the population of users, and providing the average sleep depth and a probability of a particular sleep stage over time as input to the prediction model. For example, model component 32 is configured such that a time reference (t=0 minutes) for individual sleep sessions of the population of users (e.g., whose information is part of the historical sleep depth information) is set to sleep onset (e.g., when a user actually falls asleep) in order to account for variability in sleep session start times (e.g., actual bedtimes). Model component 32 is configured to estimate the probability of a given sleep stage "S" at time "t" for the population of users by counting the number of sleep sessions of the population of users for which the sleep stage at time 't' is "S", and dividing that number by the total number of sleep sessions included in the analysis.

In some embodiments, model component 32 is configured to determine sleep onset (or sleep latency) time based on EEG information in the historical sleep depth information. In some embodiments, model component 32 is configured to determine sleep onset time based on actigraphy information and/or other information from the one or more external sleep monitoring devices included in external resources 14. In some embodiments, sleep onset during a sleep session of user 12 is determined by the one or more external sleep monitoring devices and information indicating the sleep onset time is communicated to model component 32, control component 34 (described below), and/or other components of system 10.

Figure 2A:
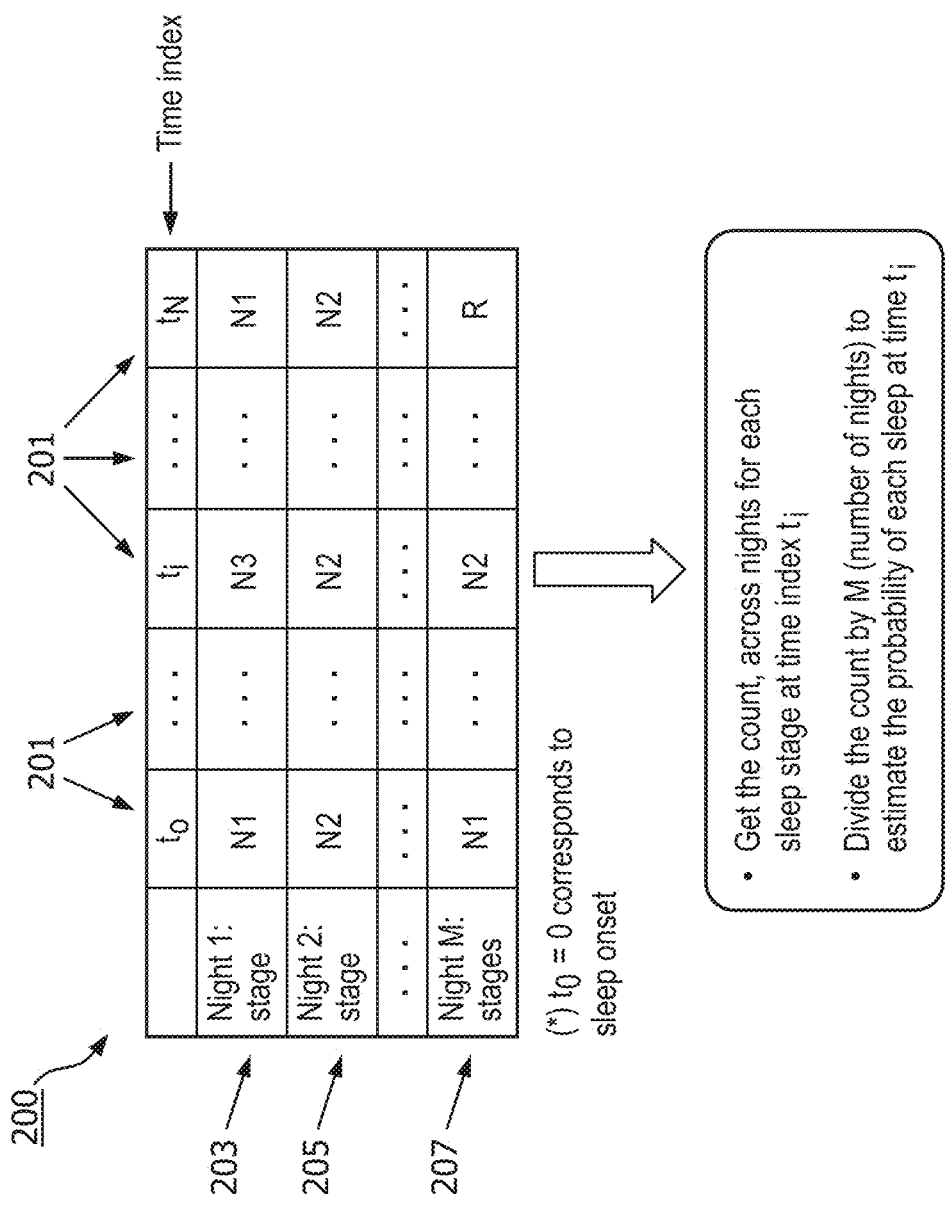
FIGS. 2A and 2B illustrate alignment of individual sleep sessions at a common time reference of a population of users whose information is part of obtained historical sleep depth information, in accordance with one or more embodiments.
Figure 2B:
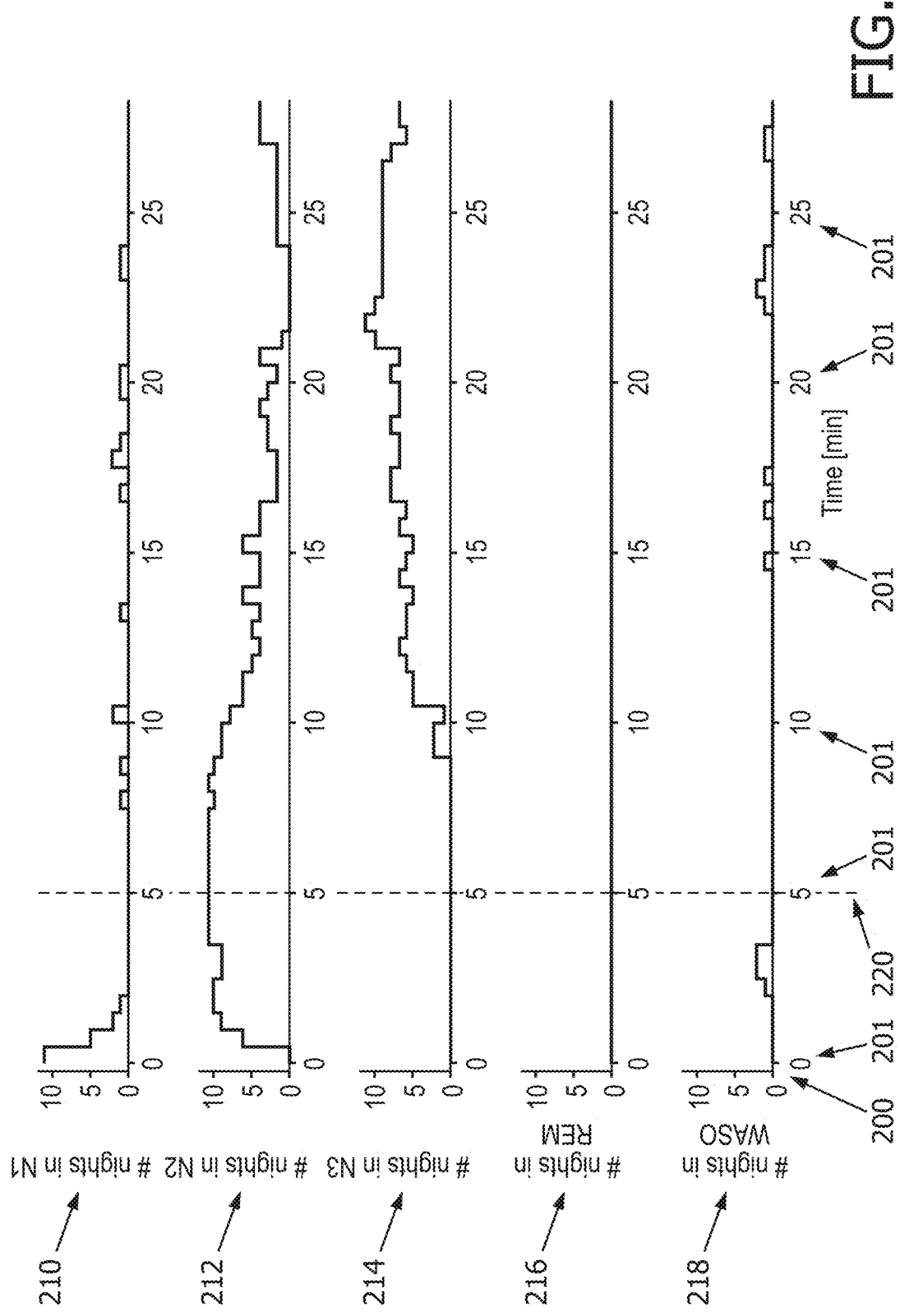

For example, FIGS. 2A and 2B illustrate alignment of individual sleep sessions of the population of users whose information is part of the historical sleep depth information at a common time reference (e.g., t=0 minutes) 200, or sleep onset time. As shown in FIG. 2A, for each time point "$t_i$" 201 (which extends from the start of a sleep session at $t_0$ to time $t_n$), the number of sleep sessions (e.g., nights) for which a given sleep stage is present at that time across the set of sleep sessions for the population of users is determined (e.g., summed). In the example shown in FIG. 2A, at time point "$t_i$" 201, a first user was in sleep stage N3 for a first sleep session 203, a second user was in sleep stage N2 for a second sleep session 205, and an Mth user was in sleep stage N2 for a sleep session 207 (but it should be noted that all three sleep sessions 203-207 could have been for a single user, for example). So at $t_i$, across this limited population/sleep session example, there were two N2 nights and one N3 night. Dividing these numbers by the total number of sleep sessions represented in the historical sleep depth information (just three in this example) gives the probability of a given sleep stage (e.g., ⅔ for N2 and ⅓ for N3 in this example) across the population of users at a given time during a sleep session. FIG. 2B is a graphical representation of the number of sleep sessions a given sleep stage (e.g., N1 210, N2 212, N3 214, REM 216, and WASO 218) was present at a given time during individual sleep sessions of the population of users. In the example shown in FIG. 2B, at time 5 minutes (labeled 220), there were no recorded instances of N1 sleep, 10 recorded instances of N2 sleep, and no recorded instances of N3, REM, or WASO. These values change as time $t_i$ 201 increases. These examples are not intended to be limiting.

Figure 3:
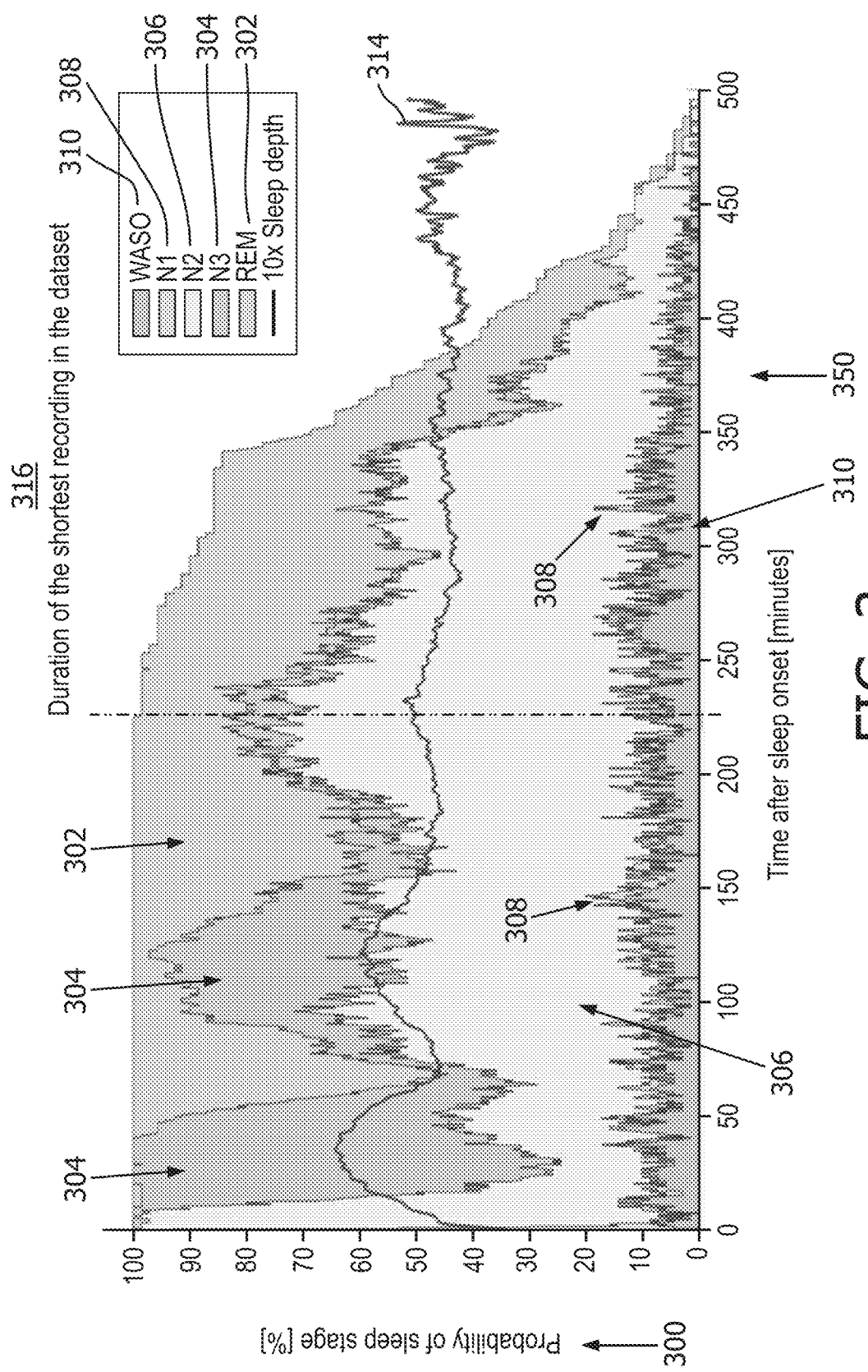
FIG. 3 illustrates a time dependent probability of individual sleep stages in a stacked manner for sleep sessions across the historical sleep depth information, in accordance with one or more embodiments.
Figure 4:
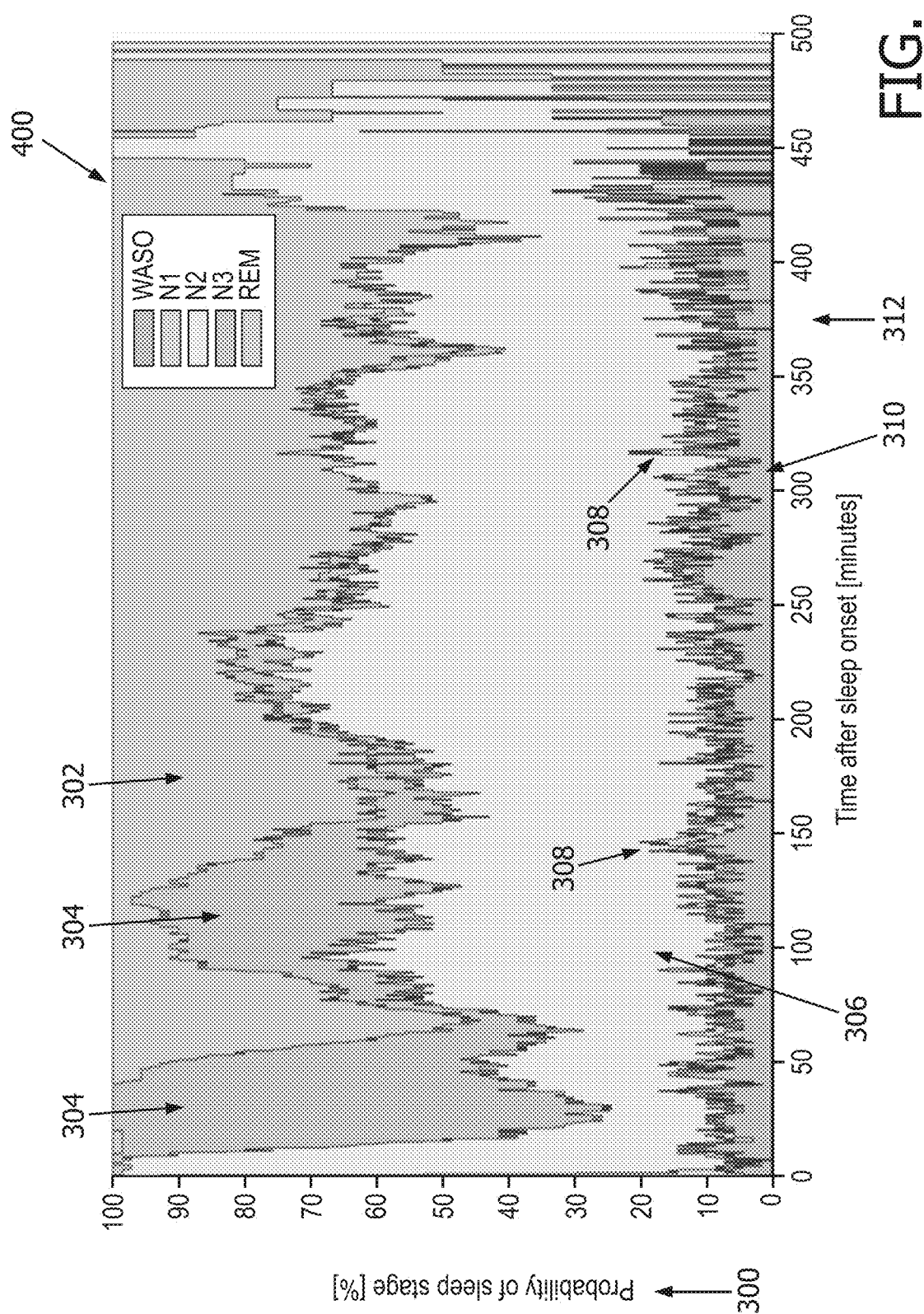
FIG. 4 illustrates normalized sleep stage probability over time for sleep sessions across the historical sleep depth information, in accordance with one or more embodiments.

For ease of visualization, FIG. 3 illustrates the probability 300 of individual sleep stages (REM 302, N3 304, N2 306, N1 308, WASO 310) over time 312 in a stacked manner across sleep sessions for example historical sleep depth information. Line 314 illustrates average sleep depth over time. It should be noted that since all (EEG) recordings in the historical sleep depth information do not necessarily have the same duration (e.g., because users wake up after different amounts of sleep), the probabilities add up to 100% up to the time 316 corresponding to the duration of the shortest recording in the dataset. In some embodiments, model component 32 (FIG. 1) is configured to normalize the sleep stage probability over time by the number of recordings available for each time point. This is illustrated in FIG. 4. However, as the number of sleep sessions decrease for times greater than 400 minutes, the reliability of the probability estimate decreases. This is illustrated in the abrupt change 400 in N2 probability 306 at around 400 minutes in FIG. 4. Typically, deep sleep occurs within 4 hours (240 minutes) after sleep onset as shown in FIG. 3 and FIG. 4. Since system 10 (FIG. 1) is configured to stimulate user 12 (FIG. 1) during deep sleep (e.g., as described herein), this probability normalization may not be necessary.

Returning to FIG. 1, model component 32 is configured such that sleep depth at a given time during a sleep session is determined based on the ratio between (1) the EEG power in a "slow" frequency band (e.g. delta (0.5 to 4 Hz) or theta (4 to 8 Hz)), and (2) the EEG power in a "fast" frequency band (e.g., alpha (8-12 Hz) or beta (15 to 30 Hz)) at that time. An example, Equation 1, is shown below. In some embodiments, one or more additional mathematical operations may be used to modify the ratios described above ($\log_2$ in this example). The average sleep depth (SD) is determined by averaging the output of Equation 1 for the plurality of sleep sessions at successive times during the sleep sessions for the population of users associated with the historical sleep depth information. Equation 1 is:

$$SD = \log_2\left(\frac{\delta}{\alpha}\right) + \log_2\left(\frac{\delta}{\beta}\right), \quad (1)$$

where $\alpha$, $\beta$, and $\delta$ are the EEG powers in the alpha, beta, and delta bands respectively for a given sleep session.

In some embodiments, model component 32 is configured such that a continuous estimation of sleep depth across sleep sessions of the historical sleep depth information is obtained by (1) band-pass filtering EEGs in the three bands (alpha, beta, and delta), squaring the result, and averaging the squared result over a one second long window, thus producing $\alpha(t)$, $\beta(t)$, and $\delta(t)$; and (2) calculating sleep depth as function of time: $SD(t)=\log_2(\delta(t)/\beta(t))+\log_2(\delta(t)/\alpha(t))$. Similar to the alignment with respect to sleep onset performed as part of determining the time dependent probability of each sleep stage (described above), model component 32 is configured to align the sleep depth determinations with respect to time for individual sleep sessions (e.g., nights) of the historical sleep depth information. In some embodiments, model component 32 is configured to average (and/or perform other mathematical operations on) the sleep depth determinations over time to determine an overall average sleep depth over time based on the historical sleep depth information. This is illustrated in FIG. 5.

Figure 5:
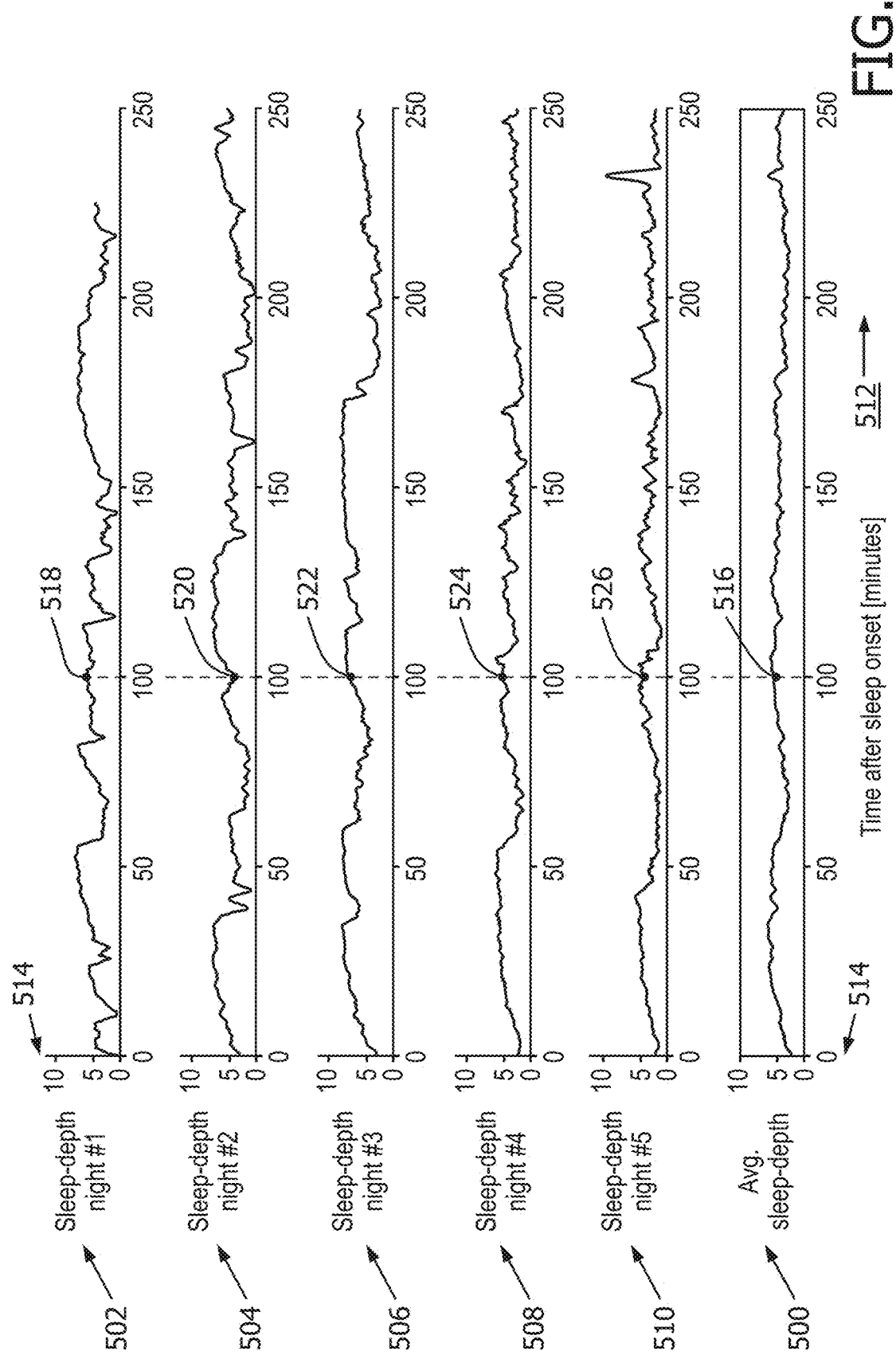
FIG. 5 illustrates average sleep depth for five separate nights of sleep whose information is included in the historical sleep depth information, in accordance with one or more embodiments.

FIG. 5 illustrates average sleep depth 500 for five separate nights (sleep sessions) 502, 504, 506, 508, and 510 of sleep. As described above, sleep depths 502-510 are determined based on EEG data included in the historical sleep depth information for the population of users. Nights 502-510 are representative of any number of nights that may be used to determine average sleep depth 500. In some embodiments, nights 502-510 may be five separate nights and/or other sleep sessions for a single user whose information is included in the historical sleep depth information. In some embodiments, nights 502-510 may be five nights of sleep for five different users whose information is included in the historical sleep depth information. As described above, average sleep depth 500 represents average sleep depth for the five (in this example) nights 502-510 over time after sleep onset 512 during the nights. For example, time zero minutes 514 corresponds to sleep onset for each of the nights 502-510. Average sleep depth 500 at a given time point 516, for example at 100 minutes, is an average of sleep depth 100 minutes (in this example) after sleep onset for each of the nights 502-510. In this example, 100 minutes after sleep onset for each of the nights is illustrated by points 518, 520, 522, 524, and 526. As shown in FIG. 5, nights (sleep sessions) 502-510 do not necessarily have the same duration. In this particular example the first 502 is shorter than the others.

Returning to FIG. 1, model component 32 is configured to cause the trained prediction model to output a time dependent predicted sleep stage for user 12 and/or the population of users whose information is included in the historical sleep depth information. The time dependent predicted sleep stage indicates whether user 12 and/or individual users in the population of users is in, or is likely to be in, deep and/or deep enough sleep for stimulation at a given time after sleep onset (e.g., deep and/or deep enough sleep that user 12 is not woken or aroused by auditory tones and/or other sensory stimulation). Conventionally sleep is characterized in terms of sleep stages NREM (N1, N2, N3) and REM. These stages provide convenience and simplify the sleep process for clinical practice. Sleep is however not a discrete, but an analog process. Sleep depth characterizes that continuum. The curve in FIG. 6 (element 612 described below) shows the continuous variation of sleep depth. In particular, sleep depth in N3 sleep is not constant. Therefore it is necessary to characterize sleep depth to determine when it is more advantageous to apply the stimulation. In some embodiments, causing the prediction model to output a time dependent predicted sleep stage for user 12 during the sleep session comprises determining whether the time dependent predicted sleep stage for a given time during the sleep session of the user is deep enough based on a corresponding average sleep depth and probability of a particular sleep stage for population of users at the given time.

Figure 6:
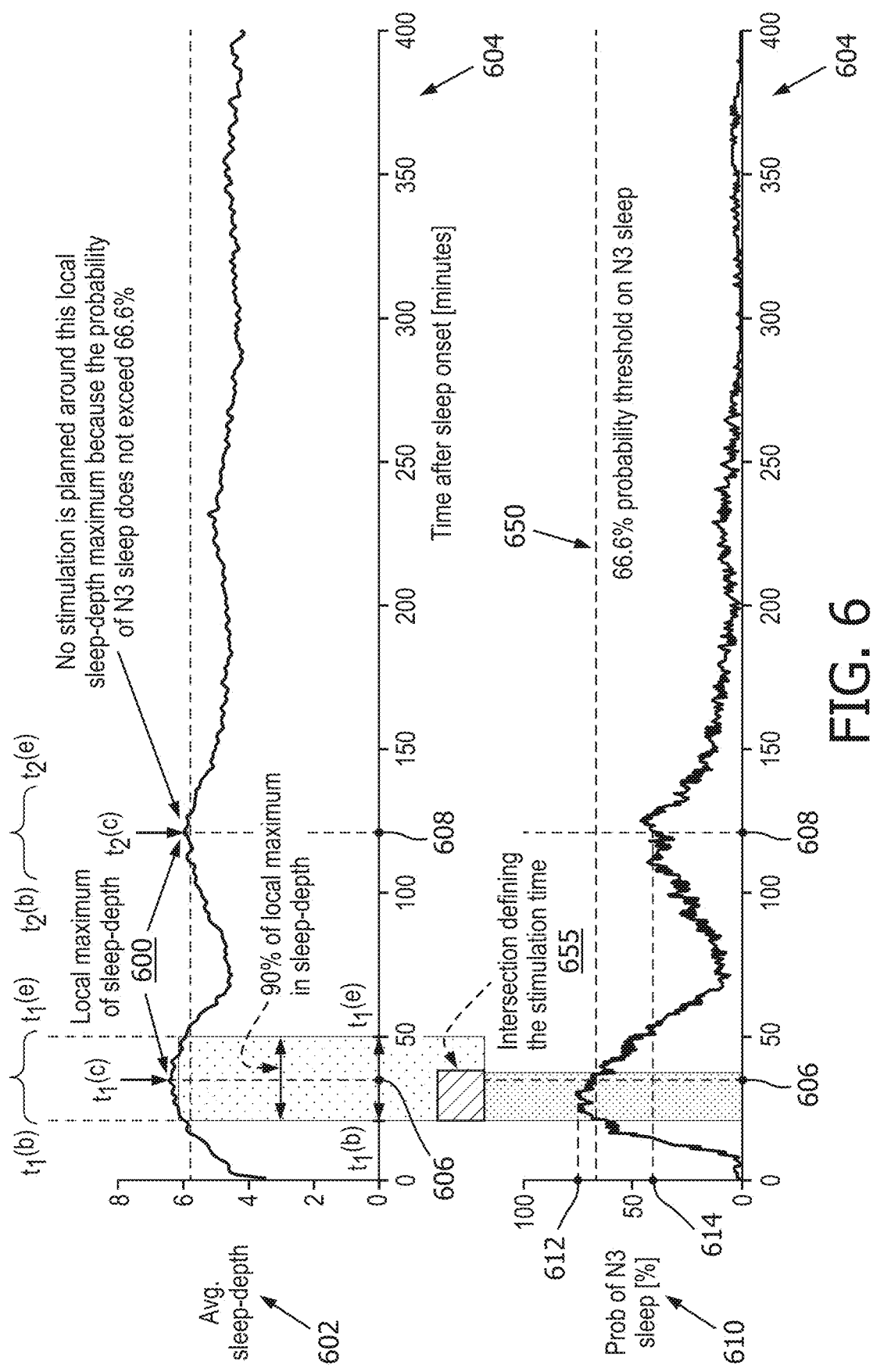
FIG. 6 illustrates determination of whether the user is in deep enough sleep for stimulation, in accordance with one or more embodiments.

FIG. 6 illustrates determination of whether user 12 (FIG. 1) is likely in deep and/or deep enough sleep for stimulation. The times after sleep onset at which it is more probable for user 12 to be in deep sleep (N3) coincide with the highest values of the average sleep depth. Model component 32 (FIG. 1) is configured such that, once the time dependent average sleep depth and probability for each sleep stage over time have been determined based on the historical sleep depth information for the population of users (e.g., as described above), the local maxima of sleep depth ($t_1^{(c)}$ and $t_2^{(c)}$) and time intervals around them are determined based on Equation 2:

$$[t_1^{(b)}; t_1^{(e)}](t_1^{(b)} < t_1^{(c)} < t_1^{(e)}), \text{ and } [t_2^{(b)}; t_2^{(e)}](t_2^{(b)} < t_2^{(c)} < t_2^{(e)}). \quad (2)$$

Local maxima 600 $t_1^{(c)}$ and $t_2^{(c)}$ of average sleep depth 602 and corresponding time intervals $t_1^{(b)}$ to $t_1^{(e)}$ and $t_2^{(b)}$ to $t_2^{(e)}$ are illustrated in FIG. 6. Model component 32 is configured to output an indication to control component 34 (FIG. 1) to cause stimulator 16 (FIG. 1) to deliver sensory stimulation to user 12 responsive to (1) a current time 604 elapsed from sleep onset for a sleep session of user 12 being within the determined intervals, and (2) a probability of N3 sleep that breaches a probability threshold at that current time. This is further described below.

In FIG. 6, the times $t_1^{(c)}$ and $t_2^{(c)}$ 606 and 608 after sleep onset that correspond to local maxima 600 of average sleep depth 602 are 35.1 minutes (606) and 121.3 minutes (608) respectively. The probability of N3 sleep 610 at times 606 and 608 is respectively 67.1% (indicated by reference numeral 612) and 37.14% (indicated by reference numeral 614). Model component 32 (FIG. 1) is configured to indicate to control component 34 (FIG. 1) that stimulation should be provided at times and/or during time intervals where average sleep-depth 602 is at least some predetermined percentage (90% in this example shown by the interval between $t_1^{(b)}$ to $t_1^{(e)}$) of a local maximum 600 of average sleep depth 602, and the probability of N3 sleep 610 breaches some predetermined probability threshold (66.6% or two thirds in this example illustrated by reference numeral 650) at that same time and/or during that same interval. In FIG. 6, for example, model component 32 and control component 34 would not cause sensory stimulator 16 (FIG. 1) to provide stimulation around the second local maximum $t_2^{(c)}$ at time 608 (e.g., 121.4 minutes) of average sleep depth 602 because the probability of finding N3 sleep at that time point is below the probability threshold used in this example. However, model component 32 and control component 34 would cause sensory stimulator 16 to provide stimulation around the first local maximum $t_1^{(c)}$ at time 606 (e.g., 35.1 minutes) at one or more times after sleep onset 604 when average sleep depth 602 is at least 90% (for example) of the local sleep depth maximum $t_1^{(c)}$ at time 606 and the probability of N3 sleep exceeds 66.6% (in this example). These time points are illustrated in FIG. 6 by box 655. The predetermined average sleep depth percentage and probability threshold values used in this example are not intended to be limiting. One or both of these parameter may have any value that allows system 10 to function as described herein. In some embodiments, one or both of these values may be determined at manufacture of system 10, entered and/or selected by user 12 and/or other operators via user interface 24 (FIG. 1) and/or other interfaces, and/or be determined in other ways.

Returning to FIG. 1, control component 34 is configured to control stimulator 16 to provide stimulation to user 12 during sleep and/or at other times. Control component 34 is configured to cause sensory stimulator 16 to provide sensory stimulation to user 12 based on an estimated sleep stage (e.g., from one or more external sleep monitoring devices included in external resources 14), a time dependent predicted sleep stage (e.g., the output from model component 32), and/or other information. Control component 34 is configured to cause sensory stimulator 16 to provide the sensory stimulation to user 12 based on an estimated sleep stage, a time dependent predicted sleep stage, and/or other information over time during the sleep session. Control component 34 is configured to cause sensory stimulator 16 to provide sensory stimulation to user 12 responsive to user 12 being in, or likely being in, deep enough sleep for stimulation (e.g., deep (N3) sleep and/or sleep as determined by model component 32 described above).

In some embodiments, control component 34 is configured to receive the estimated sleep stage (e.g., from an external sleep monitoring device via information component 30), receive the time dependent predicted sleep stage output from the prediction model (e.g., from model component 32), and control the delivery of stimulation (e.g., auditory and/or other stimulation) by stimulator 16 to control slow wave activity in user 12 based on this information. In some embodiments, control component 34 is configured such that controlling sensory stimulator 16 based on this information comprises weighting the estimated sleep stage relative to the output from the prediction model and/or other information determined and/or received by control component 34, and causing one or more sensory stimulators 16 to provide the sensory stimulation based on the weights.

In some embodiments, to balance the information from an external device and that provided by the sleep stage probability, control component 34 is configured such that the accuracy of the external device is taken into account. For example, external sleep monitoring devices may be ranked by accuracy—EEG/EOG highly accurate (0.8), ECG/PPG moderately accurate (0.6), sound monitoring during sleep (0.5), actigraphy (actiwatch) (0.3), actigraphy (mobile phone based) (0.2)—where the number in parenthesis in this example represents average accuracy (rounded up to a single digit) in detecting sleep stages. In this example, if accuracy exceeds 0.6, then control component 34 is configured such that if the external device indicates N2 or N3, stimulation is caused as per FIG. 6. Otherwise, control component 34 is configured to cause stimulation when FIG. 6 indicates deep (e.g., such that the external device will basically only inform on sleep onset).

In some embodiments, stimulators 16 are controlled by control component 34 to provide and/or adjust (e.g., optimize) stimulation at times determined as described above according to a predetermined therapy regime. Sleep slow waves can be enhanced through (e.g. peripheral auditory, magnetic, electrical, and/or other) stimulation delivered in NREM sleep (as described herein). In some embodiments, control component 34 (and/or one or more of the other processor components described herein) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

Figure 7A:
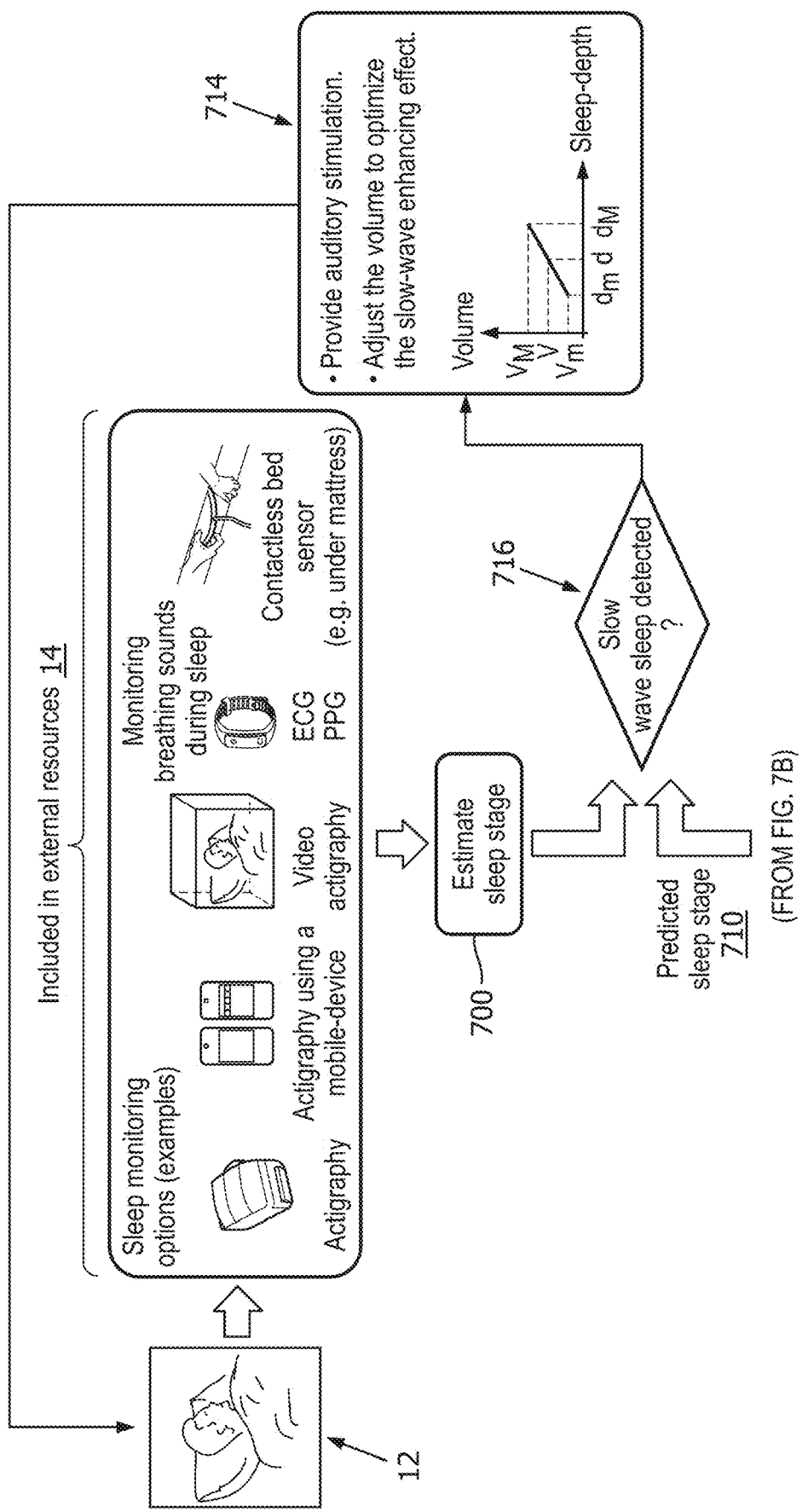
FIGS. 7A and 7B illustrate several of the operations performed by the system, in accordance with one or more embodiments.
Figure 7B:
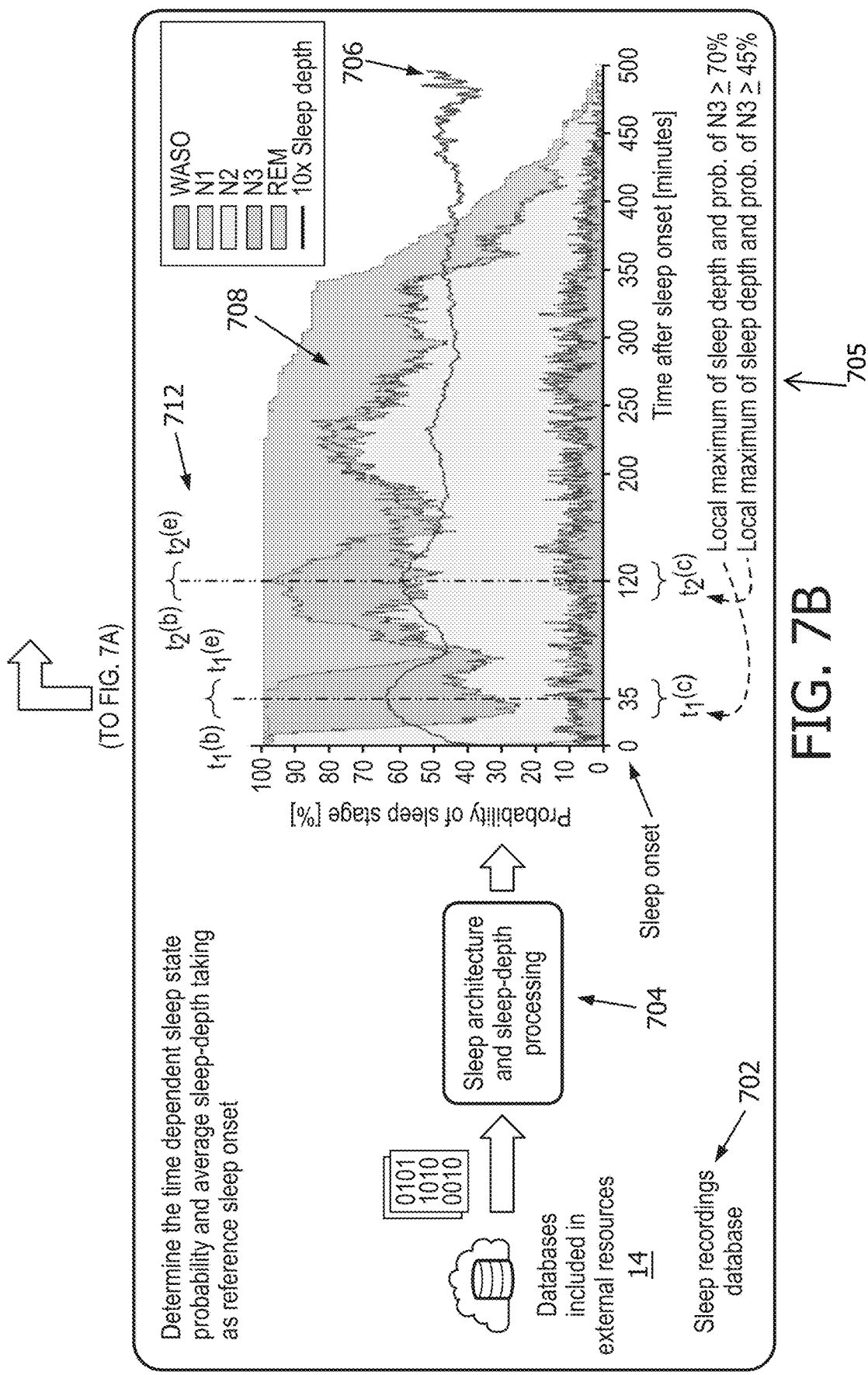

By way of a non-limiting example, FIGS. 7A and 7B several of the operations performed by system 10 (FIG. 1) described above. In FIG. 7A, one or more external sleep monitoring devices (included in external resources 14 shown in FIG. 1) monitoring user 12 output information indicating an estimated sleep stage 700. Historical sleep depth information is also obtained 702 (see FIG. 7B). The historical sleep depth information is for a population of users. The historical sleep depth information is related to brain activity of the population of users that indicates sleep depth over time during sleep sessions of the population of users. The historical sleep depth information may be obtained from one or more databases included in external resources 14 for example. As shown in FIG. 7B, a prediction model 705 is trained using the historical sleep depth information. The prediction model is trained 704 based on the historical sleep depth information by providing the historical sleep depth information as input to the prediction model. In some embodiments, causing the prediction model to be trained comprises determining average sleep depth 706 and a probability 708 of a particular sleep stage over time based on the historical sleep depth information for the sleep sessions of the population of users. The trained prediction model outputs 710 a time dependent predicted sleep stage for user 12. The time dependent predicted sleep stage indicates whether the user is in deep and/or deep enough sleep for stimulation. In some embodiments, causing the prediction model to output a time dependent predicted sleep stage for the user during the sleep session comprises determining 712 a predicted sleep stage for a given time during the sleep session of the user based on a corresponding average sleep depth and probability of a particular sleep stage for population of users at the given time. As shown in FIG. 7A, one or more sensory stimulators are caused to provide and/or adjust 714 sensory stimulation to user 12 based on the estimated sleep stage and the predicted sleep stage, and/or other information. In some embodiments, the estimated sleep stage and the predicted sleep stage indicate 716 whether user 12 is in deep enough sleep for stimulation.

Returning to FIG. 1, in some embodiments, control component 34 is configured to cause one or more sensory stimulators 16 to provide the sensory stimulation to user 12 based only on the time dependent predicted sleep stage (e.g., the output from the model) over time during the sleep session. For example, in such embodiments, one or more sensory stimulators 16 are caused to provide the sensory stimulation to user 12 responsive to the time dependent predicted sleep stage alone indicating the user is in deep and/or deep enough sleep for stimulation. Information from external sleep monitoring devices is not used. In these embodiments, model component 32 is configured to identify the times (measured from sleep onset) and/or time intervals when sleep depth is likely to be deep enough to deliver sensory stimulation (e.g., time intervals around the local maxima where the probability of N3 sleep breaches the probability threshold described related to FIG. 6 above). The stimulation is then delivered (sensory stimulator 16 is controlled by control component 34) during those intervals. As described above, sleep onset may be determined based on actigraphy, for example, and/or may also be explicitly specified by user 12 and/or other operators of system 10.

Figure 8A:
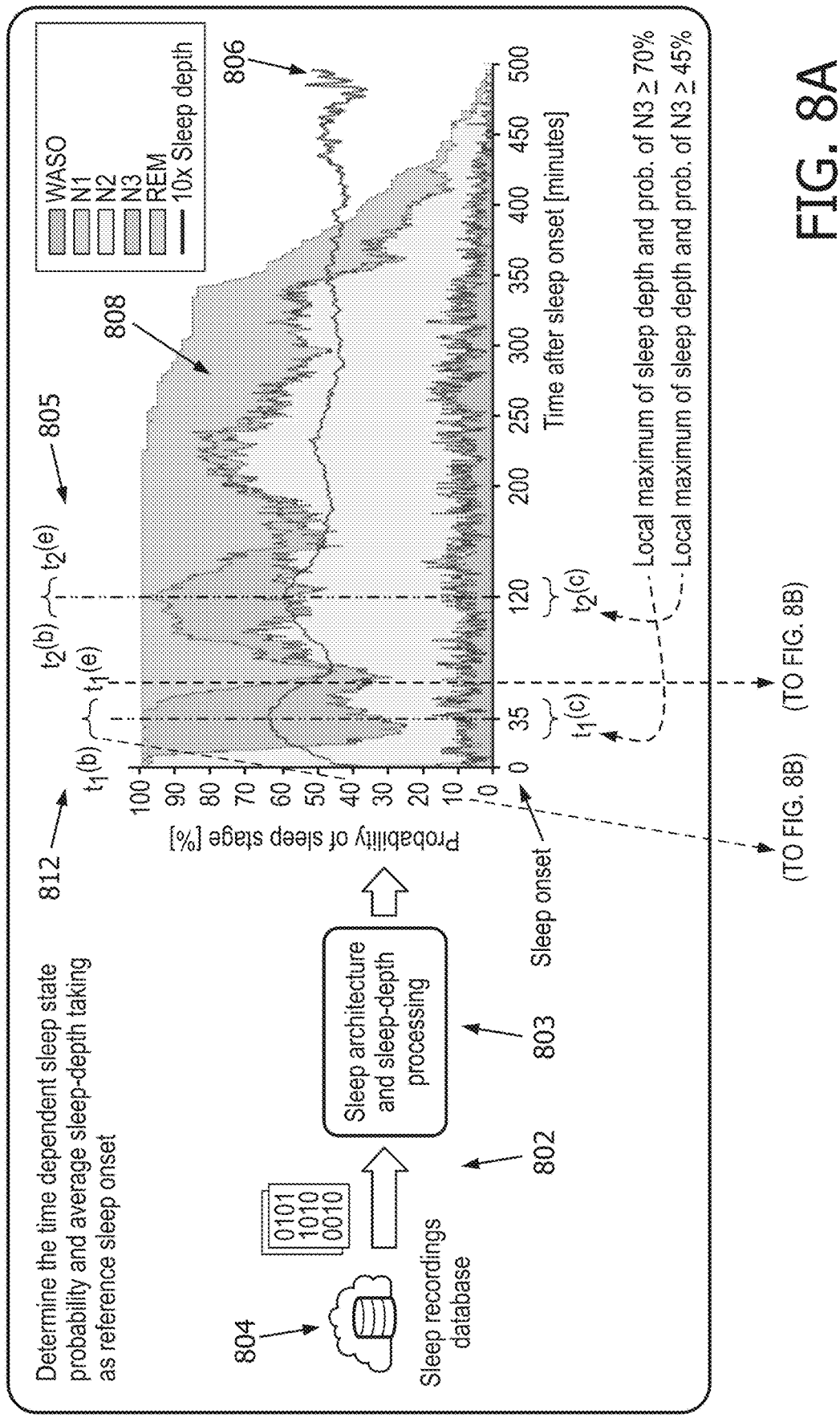
FIGS. 8A and 8B illustrate causing a sensory stimulator to provide auditory tones based on a time dependent predicted sleep stage alone, in accordance with one or more embodiments.
Figure 8B:
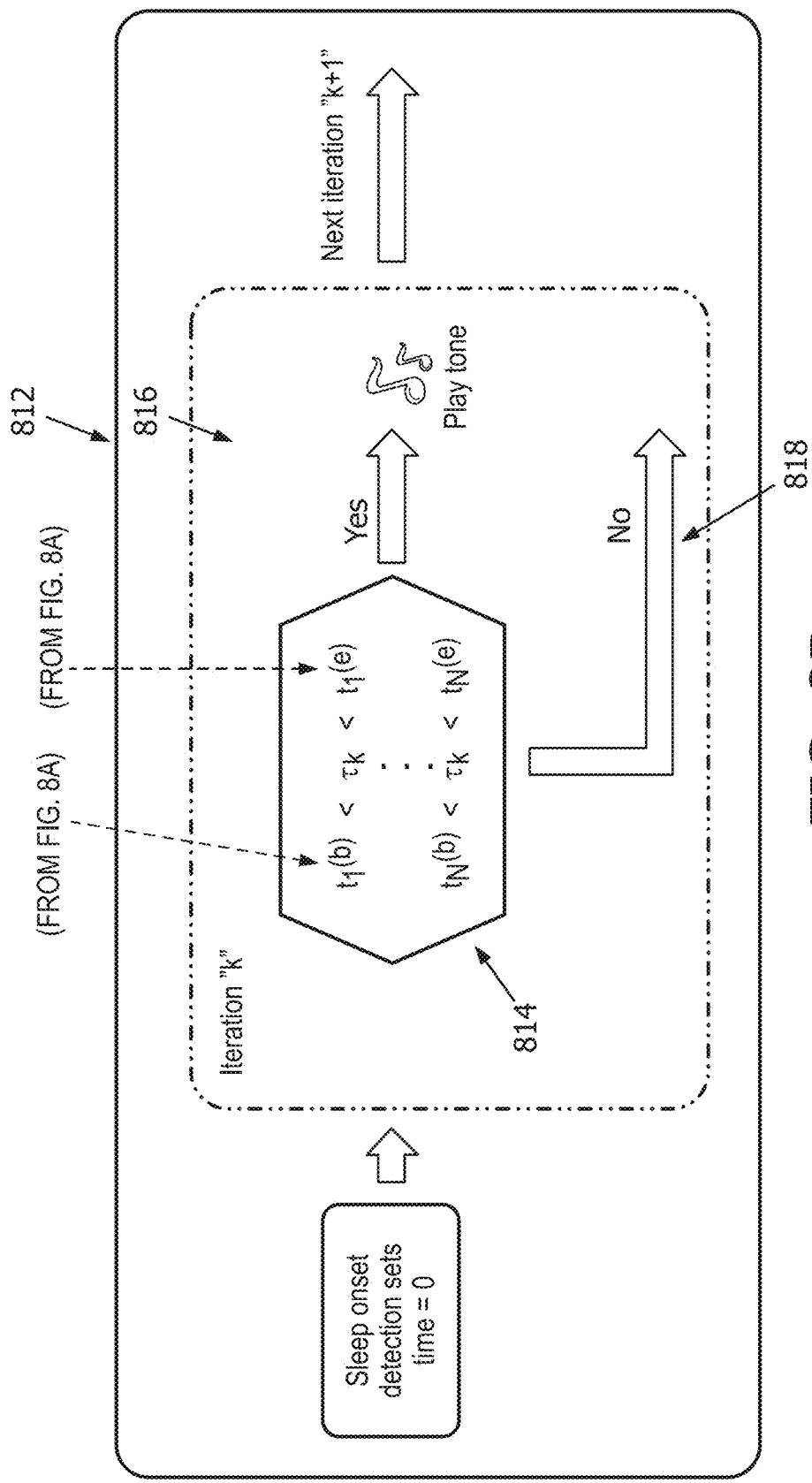

For example, FIGS. 8A and 8B illustrate causing sensory stimulator 16 (FIG. 1) to provide auditory tones based on the time dependent predicted sleep stage alone. As shown in FIG. 8A, historical sleep depth information is obtained 802. The historical sleep depth information may be obtained from one or more databases 804 included in external resources 14 (FIG. 1) for example. As shown in FIG. 8A, a prediction model 805 is trained using the historical sleep depth information. The prediction model is trained 803 based on the historical sleep depth information by providing the historical sleep depth information as input to the prediction model. In some embodiments, causing the prediction model to be trained comprises determining average sleep depth 806 and a probability 808 of a particular sleep stage over time based on the historical sleep depth information for the sleep sessions of the population of users. The trained prediction model outputs a time dependent predicted sleep stage for user 12 (FIG. 1). The time dependent predicted sleep stage indicates whether the user is in deep and/or deep enough sleep for stimulation. In some embodiments, causing the prediction model to output a time dependent predicted sleep stage for the user during the sleep session comprises determining 812 a predicted sleep stage for a given time during the sleep session of the user when user 12 is in deep and/or deep enough sleep for stimulation based on a corresponding average sleep depth and probability of a particular sleep stage for the population of users at the given time. As shown in FIG. 8B, in some embodiments, the predicted sleep stage when user 12 is in deep and/or deep enough sleep corresponds to a time and/or a time interval 814 when user 12 is in deep and/or deep enough sleep for stimulation. For example, if the probability of N3 sleep breaches a probability threshold at a time that corresponds to a local maximum in average sleep depth, tones may be delivered 816 to user 12. If not, sensory stimulation is not delivered 818 to user 12. This is similar to what is described in relation to FIG. 6 above.

Returning to FIG. 1, customization component 36 is configured to customize the prediction model for user 12. As a particular user 12 sleeps with a sleep monitoring system (e.g., with EEG sensors such as sensors 18 described herein), the system collects data that facilitates learning the typical sleep architecture for that user. In some embodiments, customizing the prediction model for user 12 includes obtaining training sleep depth information from that example system (which may or may not be system 10 with sensors 18, for example) and/or other systems and/or databases for user 12 for a plurality of sleep sessions of user 12. The training sleep depth information is related to brain activity of user 12 that indicates sleep depth over time during the plurality of sleep sessions of user 12. In some embodiments, customizing the prediction model includes re-training the prediction model based on the training sleep depth information by providing the training sleep depth information as additional input to the prediction model. In some embodiments, customizing the prediction model includes re-training the prediction model based only on the training sleep depth information by providing the training sleep depth information as the input to the prediction model (e.g., the historical sleep depth information from the population of users is not provided to the prediction model). In some embodiments, customizing the prediction model includes training the prediction model originally based only on the training sleep depth information by providing the training sleep depth information as the input to the prediction model (e.g., the historical sleep depth information from the population of users may not need to be obtained at all). In some embodiments, customizing the prediction model comprises causing the re-trained (or trained originally based only on the information related to the brain activity of user 12) prediction model to output the time dependent predicted sleep stage for user 12 during a future sleep session. In some embodiments, customizing the prediction model comprises causing one or more sensory stimulators 16 to provide the sensory stimulation to user 12 based on the time dependent predicted sleep stage over time during the future sleep session. In some embodiments, customizing the prediction model includes repeating the operations described above responsive to obtaining additional training sleep depth information for user 12.

Figure 9A:
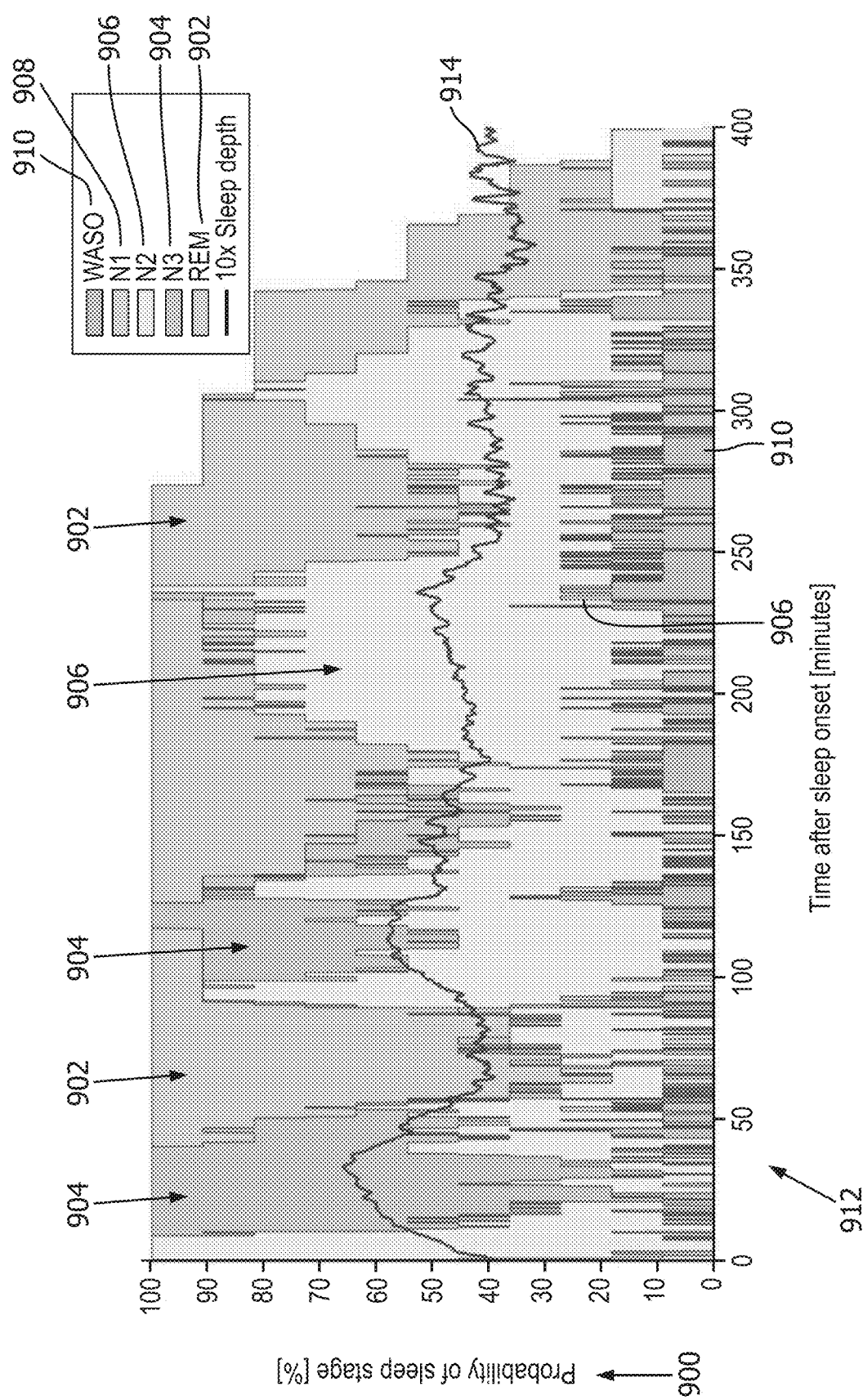
FIGS. 9A and 9B illustrate determining a time dependent predicted sleep stage for an individual user, in accordance with one or more embodiments.
Figure 9B:
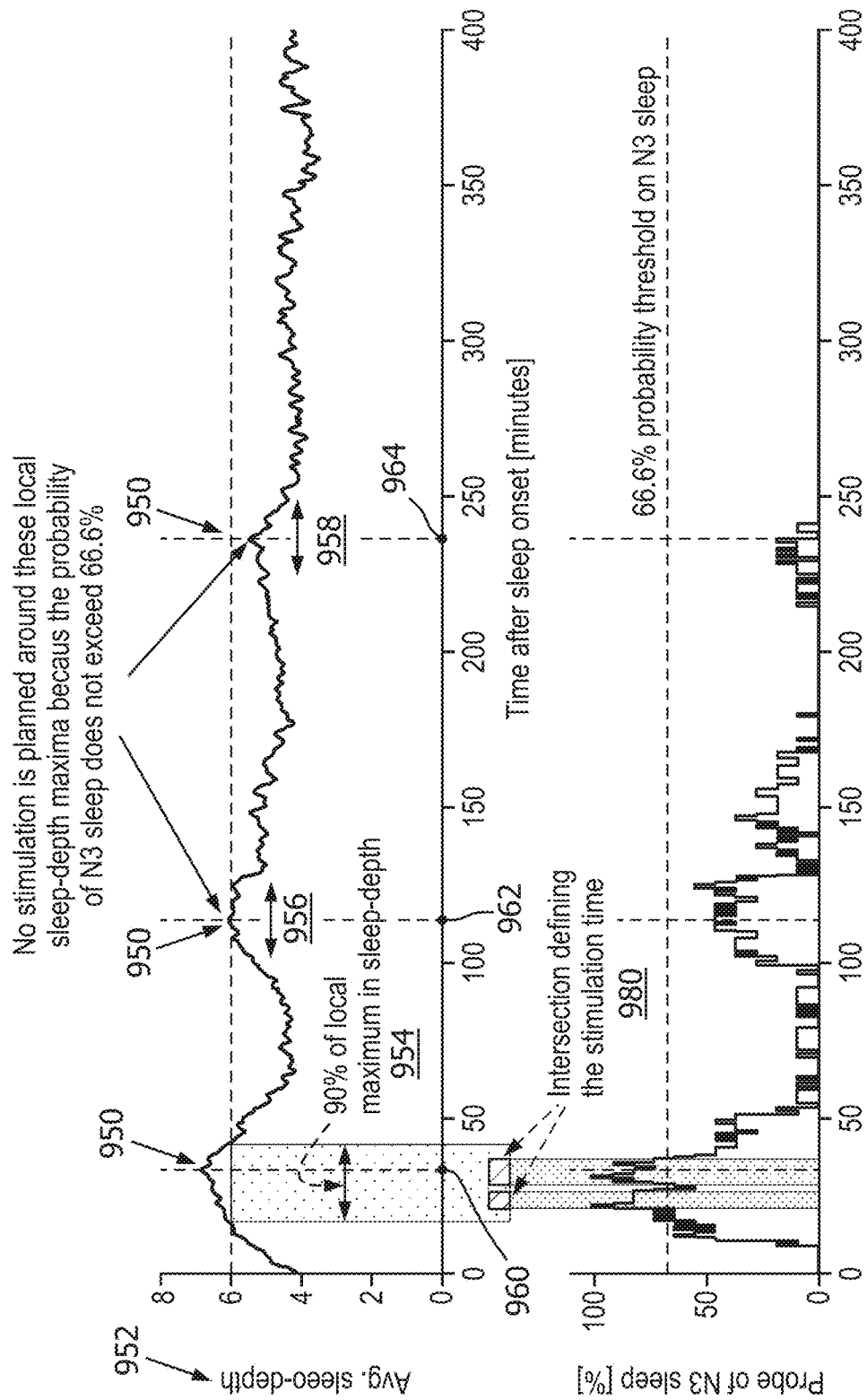

By way of a non-limiting example, FIGS. 9A and 9B illustrate determining a time dependent predicted sleep stage for an individual user 12 (FIG. 1) based on sleep depth brain activity information recorded during 11 sleep sessions. FIGS. 9A and 9B illustrate operations similar to those illustrated in FIG. 3 and FIG. 6 described above, but only for a single user. For example, FIG. 9A illustrates the probability 900 of individual sleep stages (REM 902, N3 904, N2 906, N1 908, WASO 910) over time 912 in a stacked manner across sleep sessions for example historical sleep depth information (e.g., for several nights of sleep) for the same user 12. Line 914 illustrates average sleep depth over time. In FIG. 9B, local maxima 950 of average sleep depth 952 and corresponding time intervals 954, 956, and 958 are illustrated. In FIG. 9B, the times after sleep onset that correspond to local maxima 950 of average sleep depth 952 are illustrated at 960, 962, and 964. Based on the information in FIG. 9B, for example, model component 32 (FIG. 1) and control component 34 (FIG. 1) would not cause sensory stimulator 16 (FIG. 1) to provide stimulation around the local maxima at times 962 and 964 because the probability of finding N3 sleep at that time point is below the probability threshold (e.g., 66.6%) used in this example. However, model component 32 and control component 34 would cause sensory stimulator 16 to provide stimulation around the first local maximum at time 960 because the average sleep depth 952 is at least 90% (for example) of the local sleep depth maximum 950 at time 960 and the probability of N3 sleep exceeds 66.6% (in this example). These time points are illustrated in FIG. 9B by boxes 980.

Returning to FIG. 1, in some embodiments, customization component 36 is configured such that customizing the prediction model comprises determining users similar to user 12, querying the historical sleep depth information to obtain only the information for those similar users, and training the model based on the information for the similar users. As described above, in some embodiments, the historical sleep depth information for the population of users may be: related to a user population in a given geographical area; demographic information related to gender, ethnicity, age, a general health level, and/or other demographic information; physiological information (e.g., weight, blood pressure, pulse, etc.) about the population of users, and/or other information. This information may be used by customization component 36 to determine whether an individual user in the population of users is demographically, physiologically, and/or otherwise similar to user 12.

In some embodiments, customization component 36 is configured to obtain the historical sleep depth information for similar users electronically from external resources 14, electronic storage 22, and/or other sources of information by querying one more databases and/or servers; uploading information and/or downloading information, facilitating user input (e.g., criteria used to define a target patient population input via user interface 24), sending and/or receiving emails, sending and/or receiving text messages, and/or sending and/or receiving other communications, and/or other obtaining operations. In some embodiments, customization component 36 is configured to aggregate information for the similar users from various sources (e.g., one or more of the external resources 14 described above, electronic storage 22, etc.), arrange the information in one or more electronic databases (e.g., electronic storage 22, and/or other electronic databases), normalize the information based on one or more features of the historical sleep depth information for the similar users (e.g., age, gender, geographic location, etc.) and/or perform other operations.

Advantageously, determining users similar to user 12, querying the historical sleep depth information to obtain only the information for those similar users, and training the model based on the information for the similar users may result in a prediction model that is more personalized for user 12 relative to a prediction model generated based on the historical sleep depth information for the whole population of users associated with the historical sleep depth information. This means the personalized prediction model may more accurately predict sleep stages and/or sleep stage transitions in user 12 than a model generated based on the entire historical sleep depth information dataset. Further, querying the historical sleep depth information to obtain only the information for those similar users, and training the model based on the information for the similar users, facilitates generating and training the model without having to wait to build up and/or otherwise obtain as large of a database of user data. Information from a lesser quantity of similar users may, because of the similarities between the similar users and user 12, more accurately predict the sleep behavior of user 12 compared to the information from the entire population of users associated with the historical sleep depth information.

In embodiments of system 10 that include sensor 18, sensor 18 is configured to generate output signals conveying information related to brain activity and/or other activity in user 12. In some embodiments, sensor 18 is configured to generate output signals conveying information related to brain activity such as slow wave activity in user 12. In some embodiments, the information related to brain activity and/or other activity in user 12 is the information related to slow wave activity. In some embodiments, sensor 18 is configured to generate output signals conveying information related to stimulation provided to user 12 during sleep sessions. In some embodiments, the information in the output signals from sensor 18 is used to control sensory stimulator 16 to provide sensory stimulation to user 12.

In some embodiments, the slow wave activity of user 12 may be used to detect a sleep stage of user 12. As describe above, the sleep stage of user 12 may be associated with REM sleep, NREM sleep, and/or other sleep. Sensor 18 may comprise one or more sensors that measure such sleep stages and/or other parameters directly. For example, sensor 18 may include electroencephalogram (EEG) electrodes configured to detect electrical activity along the scalp of user 12 resulting from current flows within the brain of user 12. Sensor 18 may comprise one or more sensors that generate output signals conveying information related to slow wave activity of user 12 indirectly. For example, one or more sensors 18 may comprise a heart rate sensor that generates an output based on a heart rate of user 12 (e.g., sensor 18 may be a heart rate sensor than can be located on the chest of user 12, and/or be configured as a bracelet on a wrist of user 12, and/or be located on another limb of user 12), movement of user 12 (e.g., sensor 18 may comprise an accelerometer that can be carried on a wearable, such as a bracelet around the wrist and/or ankle of user 12 such that sleep may be analyzed using actigraphy signals), respiration of user 12, and/or other characteristics of user 12.

In some embodiments, sensor 18 may comprise one or more of EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to user 12, and/or other sensors. Although sensor 18 is illustrated at a single location near user 12, this is not intended to be limiting. Sensor 18 may include sensors disposed in a plurality of locations, such as for example, within (or in communication with) sensory stimulator 16, coupled (in a removable manner) with clothing of user 12, worn by user 12 (e.g., as a headband, wristband, etc.), positioned to point at user 12 while user 12 sleeps (e.g., a camera that conveys output signals related to movement of user 12), coupled with a bed and/or other furniture where user 12 is sleeping, and/or in other locations.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, these and/or other components may be included in a headset and/or other garments worn by user 12. Such a headset may include, for example, sensing electrodes, a reference electrode, one or more devices associated with an EEG, means to deliver auditory stimulation (e.g., a wired and/or wireless audio device and/or other devices), and one or more audio speakers. In this example, the audio speakers may be located in and/or near the ears of user 12 and/or in other locations. The reference electrode may be located behind the ear of user, and/or in other locations. In this example, the sensing electrodes may be configured to generate output signals conveying information related to brain activity of user 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to user 12 via the wireless audio device and/or speakers. In this example, the sensing electrodes, the reference electrode, and the EEG devices may be represented, for example, by sensor 18 in FIG. 1. The wireless audio device and the speakers may be represented, for example, by sensory stimulator 16 shown in FIG. 1. In this example, a computing device may include processor 20, electronic storage 22, user interface 24, and/or other components of system 10 shown in FIG. 1.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 14), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of sensory stimulator 16, sensor 18, processor 20, and/or other components of system 10. For example, a hypnogram, EEG data, average sleep depth, sleep stage probability, and/or other information may be displayed for the population of users via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 10:
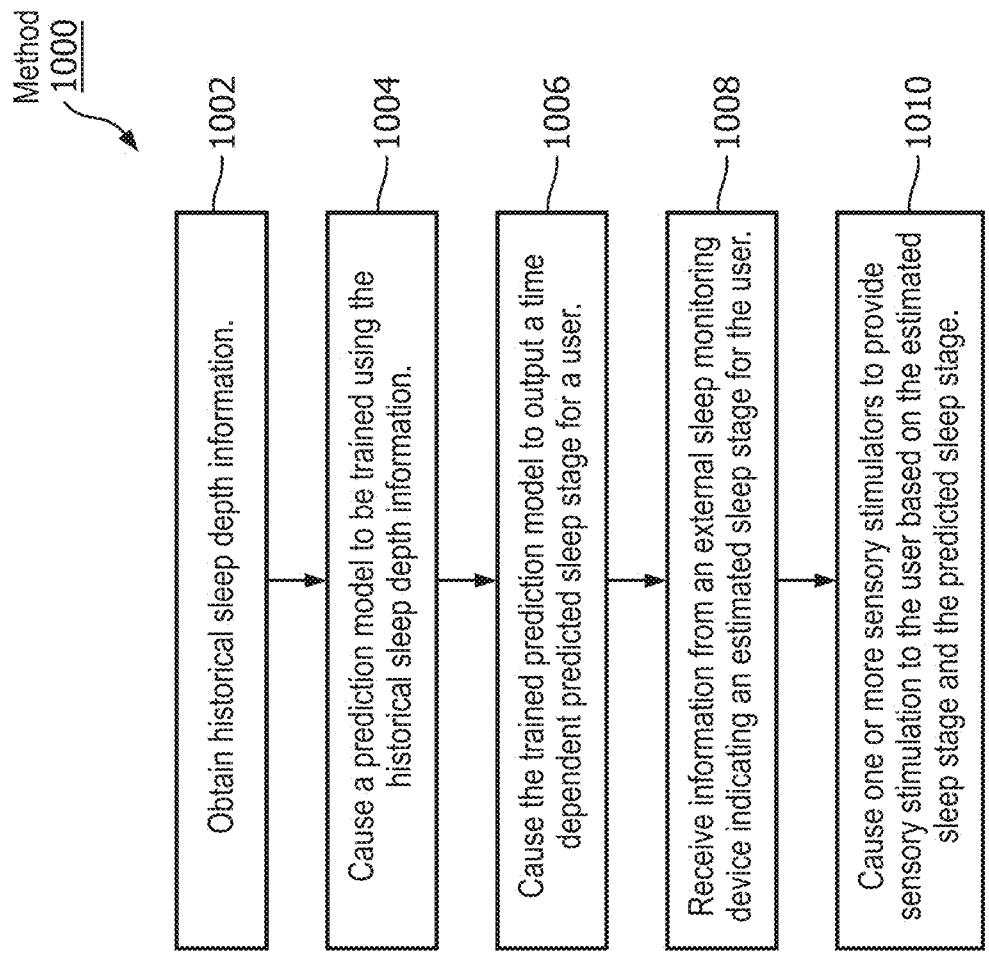
FIG. 10 illustrates a method for delivering sensory stimulation to a user during deep sleep in a sleep session, in accordance with one or more embodiments.

FIG. 10 illustrates method 1000 for delivering sensory stimulation to a user during deep sleep in a sleep session with a delivery system. The system comprises one or more sensory stimulators, one or more hardware processors configured by machine-readable instructions, and/or other components. The one or more hardware processors are configured to execute computer program components. The computer program components comprise an information component, a model component, a control component, a customization component, and/or other components. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, historical sleep depth information is obtained. The historical sleep depth information is for a population of users. The historical sleep depth information is related to brain activity of the population of users that indicates sleep depth over time during sleep sessions of the population of users. In some embodiments, operation 1002 is performed by a processor component the same as or similar to information component 30 (shown in FIG. 1 and described herein).

At an operation 1004, a prediction model is trained using the historical sleep depth information. The prediction model is trained based on the historical sleep depth information by providing the historical sleep depth information as input to the prediction model. In some embodiments, training the prediction model comprises causing the prediction model to be trained. In some embodiments, causing the prediction model to be trained comprises determining average sleep depth and a probability of a particular sleep stage over time based on the historical sleep depth information for the sleep sessions of the population of users, and providing the average sleep depth and the probability of a particular sleep stage over time as input to the prediction model. In some embodiments, operation 1004 is performed by a processor component the same as or similar to model component 32 (shown in FIG. 1 and described herein).

At an operation 1006, the trained prediction model outputs a time dependent predicted sleep stage for the user. The time dependent predicted sleep stage indicates whether the user is in deep and/or deep enough sleep for stimulation. In some embodiments, causing the prediction model to output a time dependent predicted sleep stage for the user during the sleep session comprises determining the time dependent predicted sleep stage for a given time during the sleep session of the user based on a corresponding average sleep depth and probability of a particular sleep stage for population of users at the given time. In some embodiments, operation 1006 is performed by a processor component the same as or similar to model component 32 (shown in FIG. 1 and described herein).

At an operation 1008, information from an external sleep monitoring device that indicates an estimated sleep stage of the user is received. The information from the external sleep monitoring device is received over time during the sleep session. In some embodiments, operation 1008 is performed by a processor component the same as or similar to information component 30 (shown in FIG. 1 and described herein).

At an operation 1010, the one or more sensory stimulators are caused to provide sensory stimulation to the user based on the estimated sleep stage and the predicted sleep stage, and/or other information. In some embodiments, operation 1010 includes causing the one or more sensory stimulators to provide the sensory stimulation to the user based on the estimated sleep stage and the time dependent predicted sleep stage over time during the sleep session. In some embodiments, operation 1010 comprises causing the one or more sensory stimulators to provide the sensory stimulation to the user based only on the time dependent predicted sleep stage over time during the sleep session. For example, in such embodiments, the one or more sensory stimulators are caused to provide the sensory stimulation to the user responsive to the time dependent predicted sleep stage indicating the user is in deep enough sleep for stimulation. In some embodiments, operation 1008 comprises weighting the estimated sleep stage relative to the predicted sleep stage output by the prediction model and causing the one or more sensory stimulators to provide the sensory stimulation based on the weighted estimated sleep stage and the predicted sleep stage over time during the sleep session. In some embodiments, operation 1010 is performed by a processor component the same as or similar to control component 34 (shown in FIG. 1 and described herein).

In some embodiments, method 1000 further comprises (a) obtaining, with the one or more hardware processors, training sleep depth information for the user for a plurality of sleep sessions of the user, the training sleep depth information being related to brain activity of the user that indicates sleep depth over time during the plurality of sleep sessions of user; (b) re-training, with the one or more hardware processors, the prediction model based on the training sleep depth information by providing the training sleep depth information as additional input to the prediction model; (c) causing, with the one or more hardware processors, the re-trained prediction model to output the time dependent predicted sleep stage for the user during a future sleep session; (d) causing, with the one or more hardware processors, the one or more sensory stimulators to provide the sensory stimulation to the user based on the time dependent predicted sleep stage over time during the future sleep session; and (e) repeating, with the one or more hardware processors, steps (a)-(d) responsive to obtaining additional training sleep depth information for the user. In some embodiments, these operations are performed by processor components the same as or similar to components 30-36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to deliver sensory stimulation to a user during deep sleep in a sleep session, the system comprising:

one or more sensory stimulators configured to provide sensory stimulation to the user during the sleep session;

one or more sensors configured to generate output signals conveying information related to brain activity of the user during the sleep session, the information related to brain activity of the user including information related to sleep depth of the user; and one or more hardware processors coupled to the one or more sensory stimulators, the one or more hardware processors configured by machine-readable instructions to:

determine local sleep depths for the user during the sleep session based on the output signals;

obtain historical sleep depth information for a population of users, the historical sleep depth information being related to brain activity of the population of users that indicates sleep depth over time during sleep sessions of the population of users;

cause a prediction model to be trained based on the historical sleep depth information by providing the historical sleep depth information as input to the prediction model;

cause the trained prediction model to output a time dependent predicted sleep stage for the user during the sleep session, the time dependent predicted sleep stage indicating whether the user is in deep enough sleep for stimulation;

determine the time dependent predicted sleep stage during the sleep session of the user based on a local maximum in sleep depth for the user relative to average sleep depth for the population of users, and a determination of whether a probability of a particular sleep stage for the population of users breaches a corresponding probability threshold; and cause the one or more sensory stimulators to provide the sensory stimulation to the user based on the time dependent predicted sleep stage over time during the sleep session, the one or more sensory stimulators being caused to provide the sensory stimulation to the user responsive to the time dependent predicted sleep stage indicating the user is in deep enough sleep for stimulation.

2. The system of claim 1, wherein the one or more hardware processors are further configured to receive information from an external sleep monitoring device indicating an estimated sleep stage over time for the user during the sleep session, and cause the one or more sensory stimulators to provide the sensory stimulation based on the estimated sleep stage and the predicted sleep stage over time during the sleep session.

3. The system of claim 2, wherein the one or more hardware processors are further configured to weight the estimated sleep stage relative to the predicted sleep stage output by the prediction model and cause the one or more sensory stimulators to provide the sensory stimulation based on the weighted estimated sleep stage and the predicted sleep stage over time during the sleep session.

4. The system of claim 1, wherein the one or more hardware processors are configured such that:
   causing the prediction model to be trained comprises determining, with the one or more processors, the average sleep depth and the probability of the particular sleep stage over time based on the historical sleep depth information for the sleep sessions of the population of users, and providing the average sleep depth and the probability of a particular sleep stage over time as input to the prediction model.

5. The system of claim 1, wherein the one or more hardware processors are further configured to:
   (a) obtain training sleep depth information for the user for a plurality of sleep sessions of the user, the training sleep depth information being related to brain activity of the user that indicates sleep depth over time during the plurality of sleep sessions of the user;
   (b) re-train the prediction model based on the training sleep depth information by providing the training sleep depth information as additional input to the prediction model;
   (c) cause the re-trained prediction model to output the time dependent predicted sleep stage for the user during a future sleep session;
   (d) cause the one or more sensory stimulators to provide the sensory stimulation to the user based on the time dependent predicted sleep stage over time during the future sleep session; and
   (e) repeat steps (a)-(d) responsive to obtaining additional training sleep depth information for the user.

6. A method for delivering sensory stimulation to a user during deep sleep in a sleep session with a delivery system, the system comprising one or more sensory stimulators configured to provide sensory stimulation to the user during the sleep session, one or more sensors configured to generate output signals conveying information related to brain activity of the user during the sleep session, the information related to brain activity of the user including information related to sleep depth of the user, and one or more hardware processors configured by machine-readable instructions, the method comprising:
   determining, with the one or more hardware processors, local sleep depths for the user during the sleep session based on the output signals;
   obtaining, with the one or more hardware processors, historical sleep depth information for a population of users, the historical sleep depth information being related to brain activity of the population of users that indicates sleep depth over time during sleep sessions of the population of users;
   causing, with the one or more hardware processors, a prediction model to be trained based on the historical sleep depth information by providing the historical sleep depth information as input to the prediction model;
   causing, with the one or more hardware processors, the trained prediction model to output a time dependent predicted sleep stage for the user during the sleep session, the time dependent predicted sleep stage indicating whether the user is in deep enough sleep for stimulation;
   determining the time dependent predicted sleep stage during the sleep session of the user based on a local maximum in sleep depth for the user relative to average sleep depth for the population of users and a determination of whether a probability of a particular sleep stage for the population of users breaches a corresponding probability threshold; and
   causing, with the one or more hardware processors, the one or more sensory stimulators to provide the sensory stimulation to the user based on the time dependent predicted sleep stage over time during the sleep session, the one or more sensory stimulators being caused to provide the sensory stimulation to the user responsive to the time dependent predicted sleep stage indicating the user is in deep enough sleep for stimulation.

7. The method of claim 6, further comprising receiving, with the one or more hardware processors, information from an external sleep monitoring device indicating an estimated sleep stage over time for the user during the sleep session, and causing the one or more sensory stimulators to provide the sensory stimulation based on the estimated sleep stage and the predicted sleep stage over time during the sleep session.

8. The method of claim 7, further comprising weighting, with the one or more hardware processors, the estimated sleep stage relative to the predicted sleep stage output by the prediction model and causing the one or more sensory stimulators to provide the sensory stimulation based on the weighted estimated sleep stage and the predicted sleep stage over time during the sleep session.

9. The method of claim 6, wherein:
   causing the prediction model to be trained comprises determining the average sleep depth and the probability of the particular sleep stage over time based on the historical sleep depth information for the sleep sessions of the population of users, and providing the average sleep depth and the probability of a particular sleep stage over time as input to the prediction model.

10. The method of claim 6, further comprising:
   (a) obtaining, with the one or more hardware processors, training sleep depth information for the user for a plurality of sleep sessions of the user, the training sleep depth information being related to brain activity of the user that indicates sleep depth over time during the plurality of sleep sessions of the user;
   (b) re-training, with the one or more hardware processors, the prediction model based on the training sleep depth information by providing the training sleep depth information as additional input to the prediction model;

(c) causing, with the one or more hardware processors, the re-trained prediction model to output the time dependent predicted sleep stage for the user during a future sleep session;

(d) causing, with the one or more hardware processors, the one or more sensory stimulators to provide the sensory stimulation to the user based on the time dependent predicted sleep stage over time during the future sleep session; and (e) repeating, with the one or more hardware processors, steps (a)-(d) responsive to obtaining additional training sleep depth information for the user.

11. A system for delivering sensory stimulation to a user during deep sleep in a sleep session, the system comprising:

means for providing sensory stimulation to the user during the sleep session;

means for generating output signals conveying information related to brain activity of the user during the sleep session, the information related to brain activity of the user including information related to sleep depth of the user;

means for determining local sleep depths for the user during the sleep session based on the output signals;

means for obtaining historical sleep depth information for a population of users, the historical sleep depth information being related to brain activity of the population of users that indicates sleep depth over time during sleep sessions of the population of users;

means for causing a prediction model to be trained based on the historical sleep depth information by providing the historical sleep depth information as input to the prediction model;

means for causing the trained prediction model to output a time dependent predicted sleep stage for the user during the sleep session, the time dependent predicted sleep stage indicating whether the user is in deep enough sleep for stimulation;

means for determining the time dependent predicted sleep stage during the sleep session of the user based on a local maximum in sleep depth for the user relative to average sleep depth for the population of users, and a determination of whether a probability of a particular sleep stage for the population of users breaches a corresponding probability threshold; and means for causing the means for providing sensory stimulation to provide the sensory stimulation to the user based on the time dependent predicted sleep stage over time during the sleep session, the means for providing sensory stimulation being caused to provide the sensory stimulation to the user responsive to the time dependent predicted sleep stage indicating the user is in deep enough sleep for stimulation.

12. The system of claim 11, further comprising means for receiving information from an external sleep monitoring device indicating an estimated sleep stage over time for the user during the sleep session, and causing the means for generating sensory stimulation to provide the sensory stimulation based on the estimated sleep stage and the predicted sleep stage over time during the sleep session.

13. The system of claim 12, further comprising means for weighting the estimated sleep stage relative to the predicted sleep stage output by the prediction model and causing the means for generating sensory stimulation to provide the sensory stimulation based on the weighted estimated sleep stage and the predicted sleep stage over time during the sleep session.

14. The system of claim 11, wherein:

causing the prediction model to be trained comprises determining the average sleep depth and the probability of the particular sleep stage over time based on the historical sleep depth information for the sleep sessions of the population of users, and providing the average sleep depth and the probability of a particular sleep stage over time as input to the prediction model.

15. The system of claim 11, further comprising:

(a) means for obtaining training sleep depth information for the user for a plurality of sleep sessions of the user, the training sleep depth information being related to brain activity of the user that indicates sleep depth over time during the plurality of sleep sessions of the user;

(b) means for re-training the prediction model based on the training sleep depth information by providing the training sleep depth information as additional input to the prediction model;

(c) means for causing the re-trained prediction model to output the time dependent predicted sleep stage for the user during a future sleep session;

(d) means for causing the means for generating sensory stimulation to provide the sensory stimulation to the user based on the time dependent predicted sleep stage over time during the future sleep session; and (e) means for repeating steps (a)-(d) responsive to obtaining additional training sleep depth information for the user.

* * * * *